US007119187B2

(12) United States Patent
Lee et al.

(10) Patent No.: US 7,119,187 B2
(45) Date of Patent: Oct. 10, 2006

(54) INTERNAL RIBOSOME ENTRY SITE OF THE LABIAL GENE FOR PROTEIN EXPRESSION

(75) Inventors: Dung-Fang Lee, Tainan (TW); Jyh-Lyh Juang, Taipei (TW)

(73) Assignee: National Health Research Institutes, Miaoli (TW)

( * ) Notice: Subject to any disclaimer, the term of this patent is extended or adjusted under 35 U.S.C. 154(b) by 0 days.

(21) Appl. No.: 10/614,282

(22) Filed: Jul. 8, 2003

(65) Prior Publication Data

US 2004/0082034 A1 Apr. 29, 2004

Related U.S. Application Data

(60) Provisional application No. 60/394,270, filed on Jul. 9, 2002.

(51) Int. Cl.
*C07H 21/04* (2006.01)
(52) U.S. Cl. .................................................. 536/23.1
(58) Field of Classification Search ................ 536/23.1
See application file for complete search history.

(56) References Cited

U.S. PATENT DOCUMENTS

| 4,745,051 | A | 5/1988 | Smith et al. ................... 435/68 |
| 4,879,236 | A | 11/1989 | Smith et al. ................. 435/235 |
| 5,147,788 | A | 9/1992 | Page et al. .................. 435/69.1 |

OTHER PUBLICATIONS

Goswami et al. (2003, Journal of Molecular Evolution, 57:44-51).*
Mlodzik, et al. 1988, The EMBO Journal, 7: 2569-2578.*
Technical Services, 1993, Promega Catalog, see NCBI printout, gi No.: 58196.*
U.S. Appl. No. 10/614,283, filed Jul. 8, 2003, Hsu et al.
Bonneau, A.M. et al., "Involvement of the 24-kDa Cap-binding Protein in Regulation of Protein Synthesis in Mitosis," *J. Biol. Chem.*, 262:11134-11139 (1987).
Borman, A. et al., "The involvement of a spliceosome component in internal initiation of human rhinovirus RNA translation," *J. Gen. Virol.*, 74:1775-1788 (1993).
Creancier, L. et al., "c-myc Internal Ribosome Entry Site Activity Is Developmentally Controlled and Subjected to a Strong Translational Repression in Adult Transgenic Mice," *Mol. Cell. Biol.*, 21:1833-1840 (2001).
Dansereau, D. et al., "*ectopic margin (ema)* is required for refinement of Notch activity at the D/V boundary of the wing," 42nd Ann. *Drosophila* Res. Conf., abstr. 532A (2001).
Davis, M. et al., "Role of polypyrimidine tract binding (PTB) protein during Drosophila development," 42nd Ann. *Drosophila* Res. Conf., abstr. 357C (2001).
Finkelstein, Y. et al., "The use of bi-cistronic transfer vectors for the baculovirus expression system," *J. Biotech.*, 75:33-44 (1999).
Gurtu, V. et al., "IRES Bicistronic Expression Vectors for Efficient Creation of Stable Mammalian Cell Lines," *Biochem. Biophys. Res. Comm.* 229:295-298 (1996).

Huang, J.T. et al., "Adenovirus Inhibition of Cellular Protein Synthesis Involves Inactivation of Cap Binding Protein," *Cell*, 65:271-280 (1991).
Hennecke, M. et al., "Composition and arrangement of genes define the strength of IRES-driven translation in bicistronic mRNAs," *Nucleic Acids Res.*, 29:3327-3334 (2001).
Holcik, M. et al., "Functional Characterization of the X-Linked Inhibitor of Apoptosis (XIAP) Internal Ribosome Entry Site Element: Role of La Autoantigen in XIAP Translation," *Mol. Cell. Biol.*, 20:4648-4657 (2000).
Jang, S.K. et al., "Cap-independent translation of encephalomyocarditis virus RNA: structural elements of the internal ribosomal entry site and involvement of a cellular 57-kD RNA-binding protein," *Genes Dev.*, 4:1560-1572 (1990).
Kim, Y.K. et al., "Polypyrimidine Tract-binding Protein Inhibits Translation of Bip mRNA," *J. Mol. Biol.*, 304:119-133 (2000).
Le, S.-Y. et al., "A common RNA structural motif involved in the internal initiation of translation of cellular mRNAs," *Nucleic Acids Res.*, 25:362-369 (1997).
Luckow V.A. et al., "Trends in the Development of Baculovirus Expression Vectors," *Bio/Technology*, 6:47-55 (1988).
Luckow, V.A. "Cloning and Expresion of Heterologous Genes in Insect Cells with Baculovirus Vectors," In: *Recombinant DNA Technology and Applications*, McGraw-Hill, New York, pp. 97-152 (1991).
Macajak, D.G. et al., "Internal initiation of translation mediated by the 5' leader of a cellular mRNA," *Nature*, 353:90-94 (1991).
Miller, L.K. "Baculoviruses as Gene Expression Vectors," *Annu. Rev. Microbiol.*, 42:177-199 (1988).
Mitchell, S.A. et al., "Protein Factor Requirements of the Apaf-1 Internal Ribosome Entry Segment: Roles of Polypyrimidine Tract Binding Protein and upstream of N-ras," *Mol. Cell. Biol.*, 21:3364-3374 (2001).
Oh, S.-K. et al., "Homeotic gene *Antennapedia* mRNA contains 5'-noncoding sequences that confer translational initiation by internal ribosome binding," *Genes Dev.*, 6:1643-1653 (1992).
Oumard A. et al., "Translation of NRF mRNA is Mediated by Highly Efficient Internal Ribosome Entry," *Mol. Cell. Biol.*, 20:2755-2759 (2000).
Paz, I. et al., "Starved *Saccharomyces cerevisiae* Cells Have the Capacity to Support Internal Initiation of Translation," *J. Biol. Chem.*, 274:21741-21745 (1999).
Pelletier, J. et al., "Internal initiation of translation of eukaryotic mRNA directed by a sequence derived from poliovirus RNA," *Nature*, 334:320-325 (1988).
Pozner, A. et al., "Transcription-Coupled Translation Control of AML1/RUNX1 is Mediated by Cap- and Internal Ribosome Entry Site-Dependent Mechanisms," *Mol. Cell. Biol.*, 20:2297-2307 (2000).
Saleh, L. et al., "Functional interaction of translation initiation factor eIF4G with the foot-and-mouth disease virus internal ribosome entry site," *J. Gen. Virol.*, 82:757-763 (2001).

(Continued)

*Primary Examiner*—Dave Trong Nguyen
*Assistant Examiner*—Joanne Hama
(74) *Attorney, Agent, or Firm*—Finnegan, Henderson, Farabow, Garrett & Dunner, L.L.P.

(57) ABSTRACT

The invention describes compositions and methods for recombinant protein expression in a wide range of cell types. The compositions comprise an IRES sequence from the *Drosophila labial* (lab) gene, or a variant or fragment thereof, or alternatively, a homolog of a lab IRES, or a variant or fragment thereof. Methods of using the compositions are also described.

16 Claims, 24 Drawing Sheets

OTHER PUBLICATIONS

Sarnow, P. "Translation of glucose-regulated protein 78/immunoglobulin heavy-chain binding protein mRNA is increased in poliovirus-infected cells at a time when cap-dependent translation of cellular mRNAs is inhibited," *PNAS*, 86:5795-5799 (1989).

Stoneley, M. et al., "C-Myc 5' untranslated region contains an internal ribosome entry segment," *Oncogene*, 16:423-428 (1998).

Vagner, S. et al., "Alternative Translation of Human Fibroblast Growth Factor 2 mRNA Occurs by Internal Entry of Ribosomes," *Mol. Cell. Biol.*, 15:35-44 (1995).

Woolaway K.E. et al., "The 5' Untranslated Region of *Rhopalosiphum padi* Virus Contains an Internal Ribosome Entry Site Which Functions Efficiently in Mammalian, Plant, and Insect Translation Systems," *J. Virol.* 75:10244-10249 (2001).

Ye, X. et al., "*Ultrabithorax* and *Antennapedia* 5' Untranslated Regions Promote Developmentally Regulated Internal Translation Initiation," *Mol. Cell. Biol.*, 17:1714-1721 (1997).

Zhou, W. et al., "Transcript leader regions of two *Saccharomyces cerevisiae* mRNAs contain internal ribosome entry sites that function in living cells," *PNAS*, 98:1531-1536 (2001).

Zuker, M. "Computer Prediction of RNA Structure," *Methods Enzymol.*, 180:262-288 (1989).

Invitrogen Life Sciences Catalog Description for the pcDNA3.1/ His© A, B, and C vector, Catalog No. V385-20, Version E, Invitrogen Corp. 1997-2001, pp. i-14.

\* cited by examiner

FIG. 1A   Lab 5'UTR

```
  1  atcagtcacg acttggtaag cgcgcaggca gcacgtcgtc gtcgtcatcg
 51  ccaacgggag tcgtgttttt cggttcgata cagataaaac ccacgtcgat
101  agccctcgac cgtcgcgtaa tattcttaga aagcaaacag ctaaagaact
151  atttcaagaa ctgtgtggca agtgaagggt agttagtgat acaccggtta
201  tatcggagtg gcgagaaagt gtggttccgg ctggacaat
```

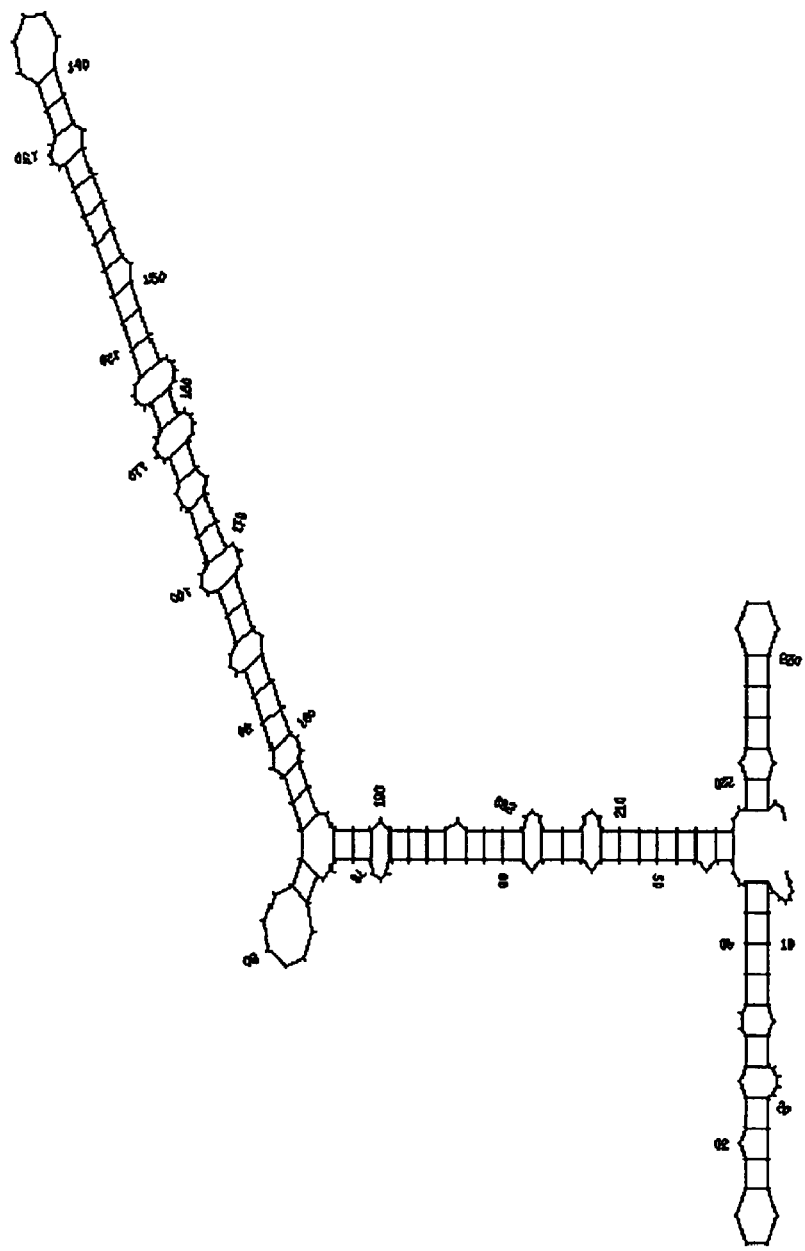

pAcGalLuc    pAcGal*EMCV*Luc    pAcGal*Antp*Luc    pAcGal*Lab*Luc

FIG. 2F
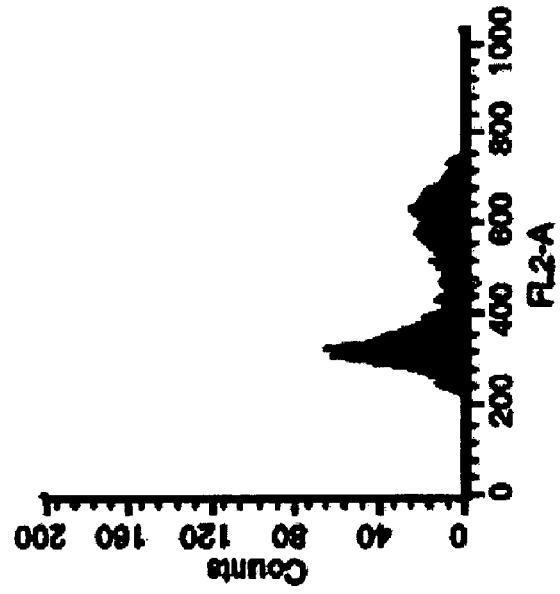
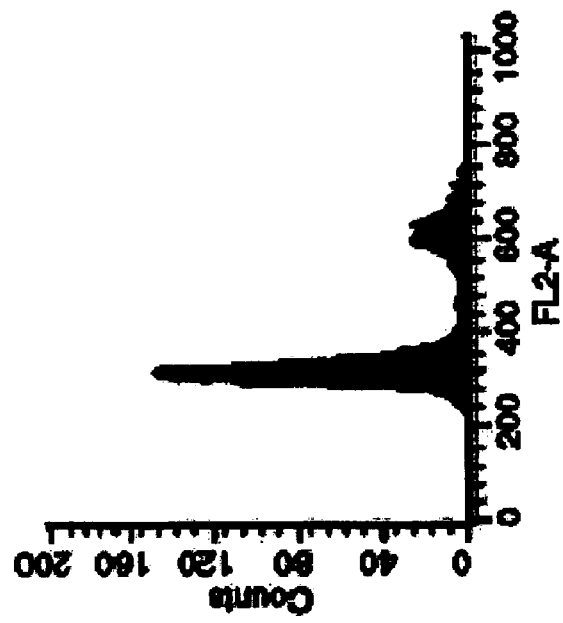

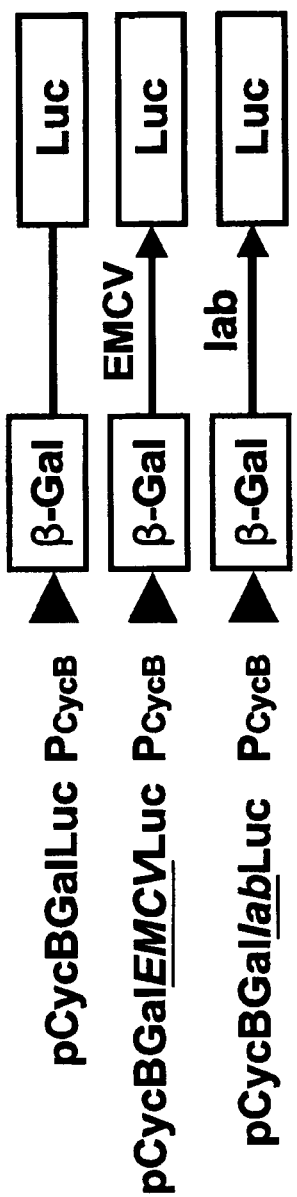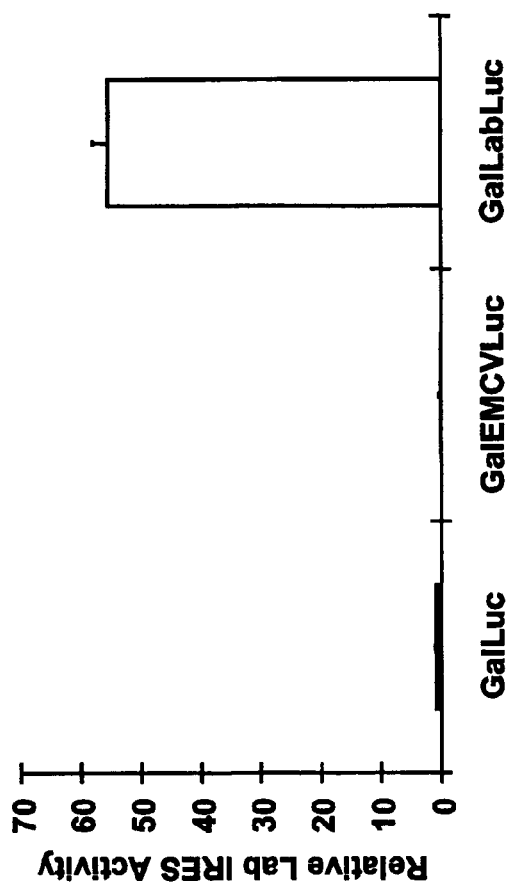
FIG. 2H

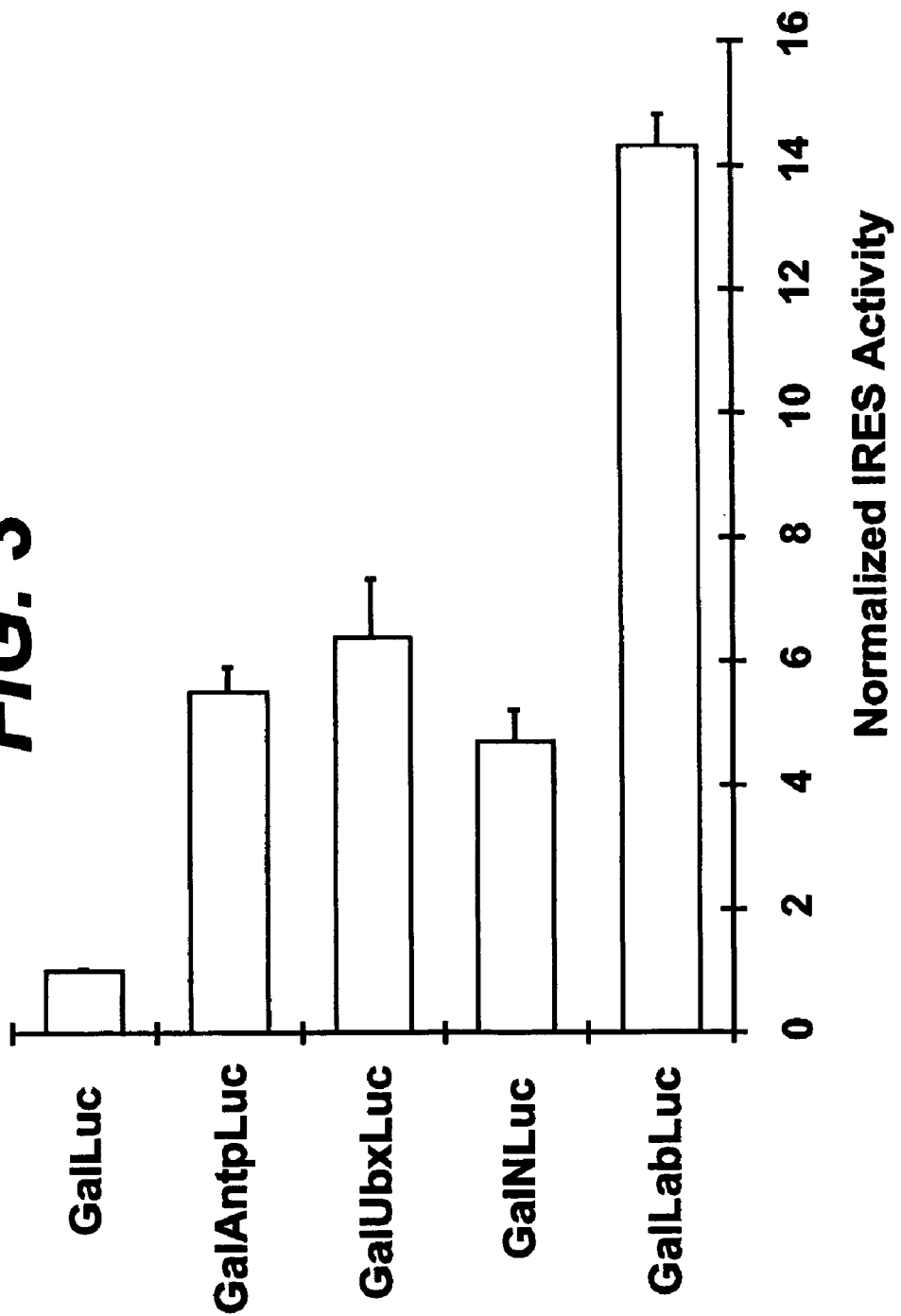

FIG. 4A Homeobox A1 5'UTR

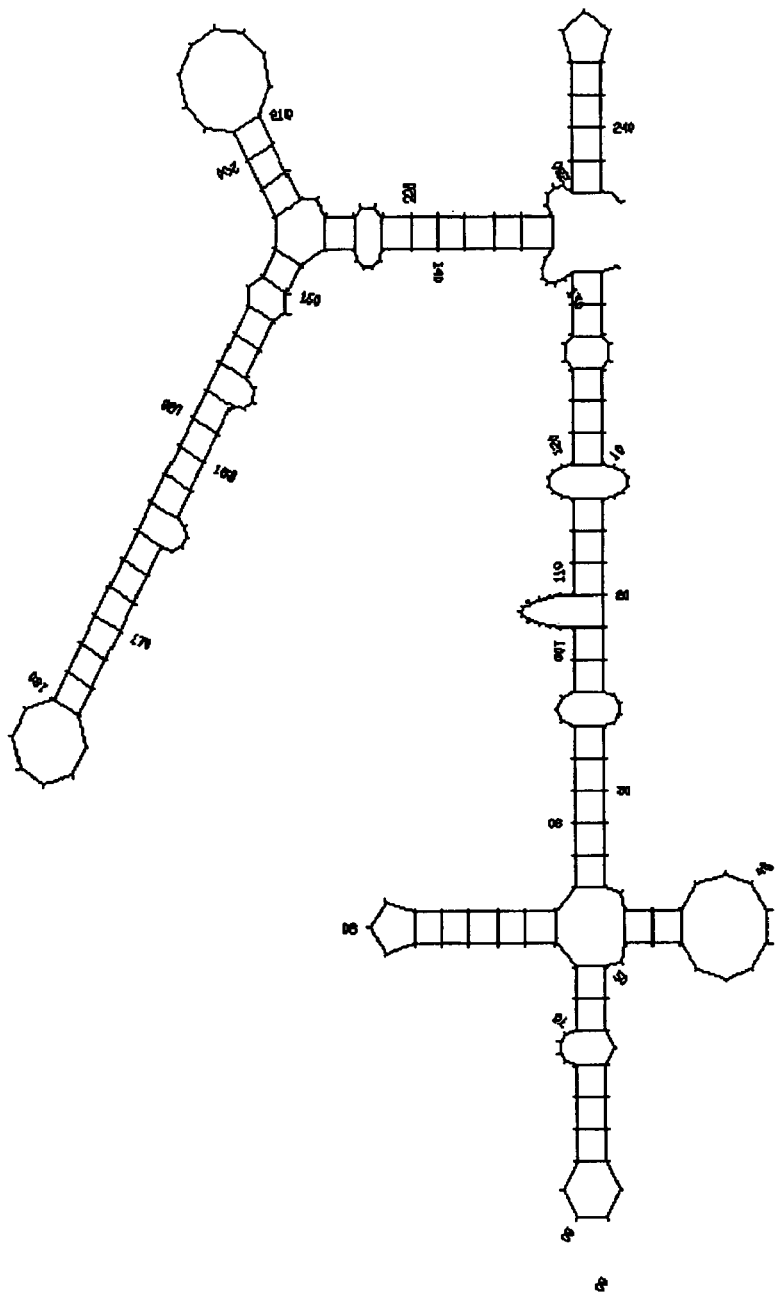
FIG. 4B Secondary Structure

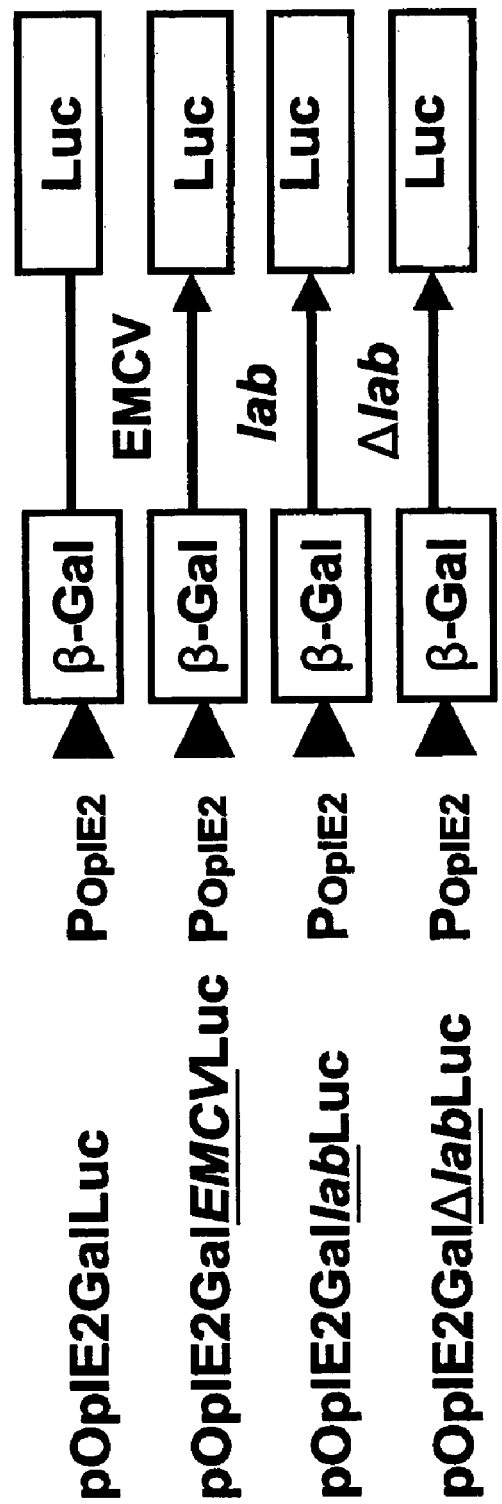

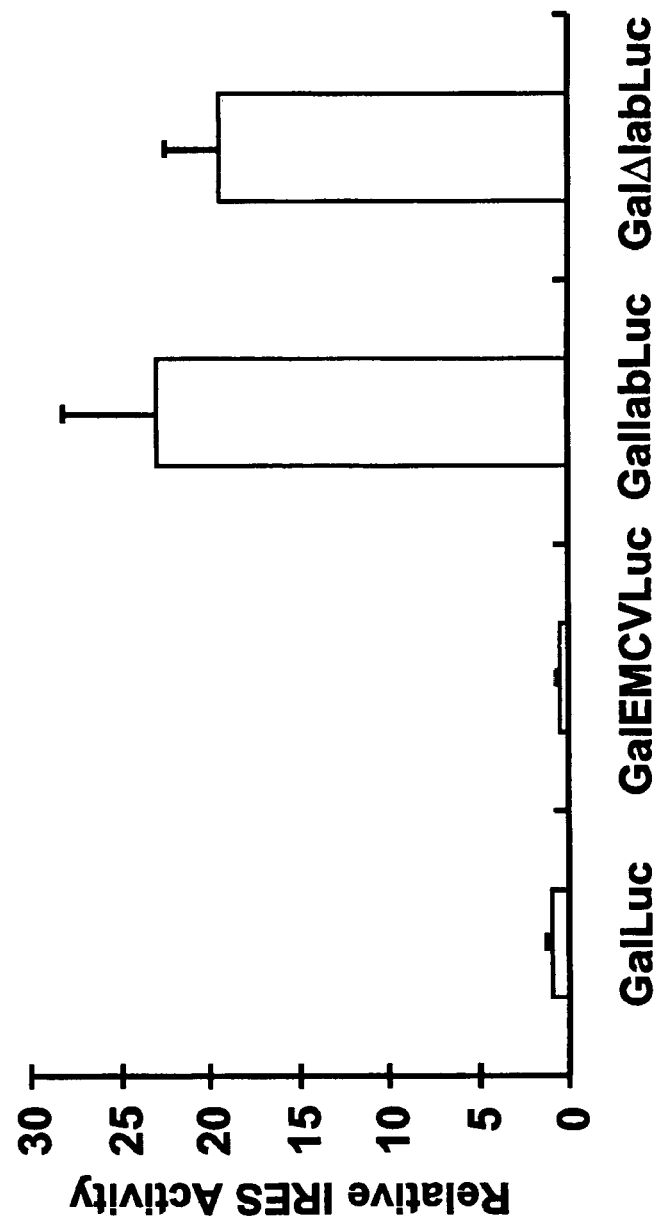

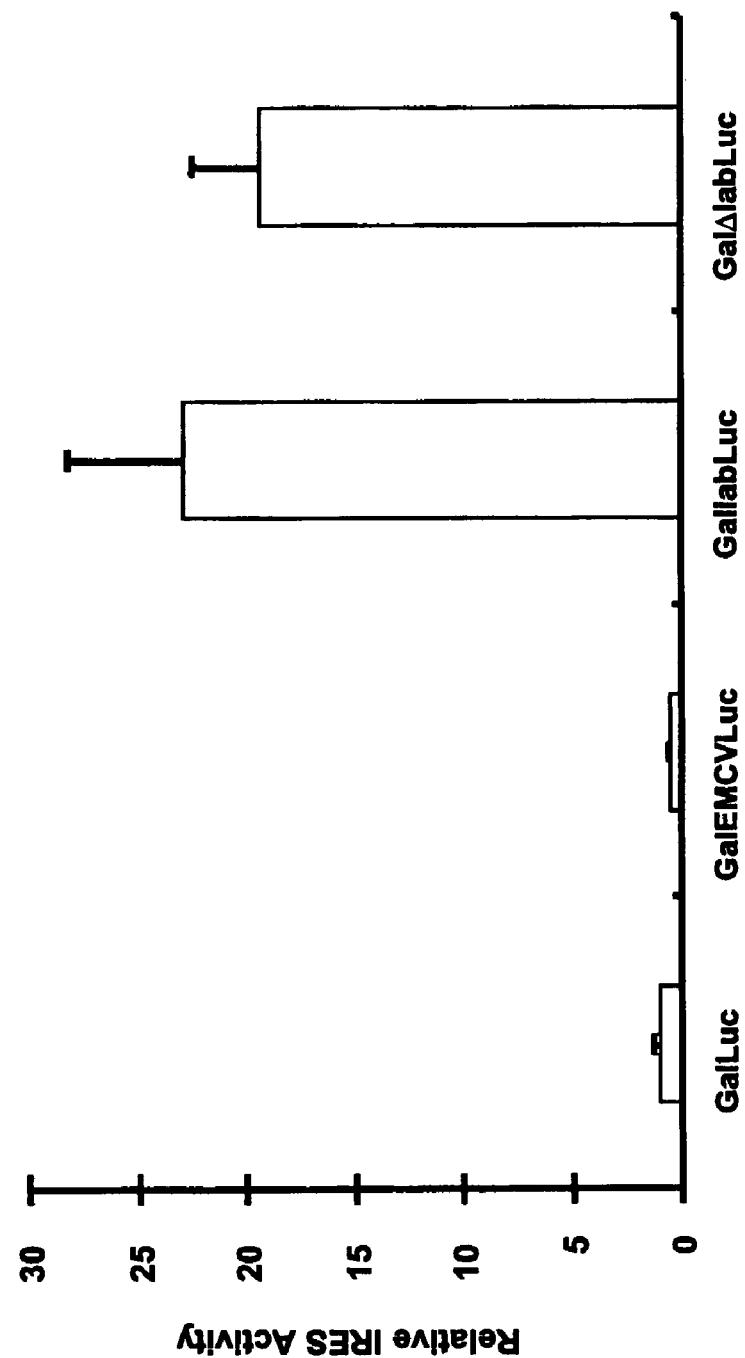

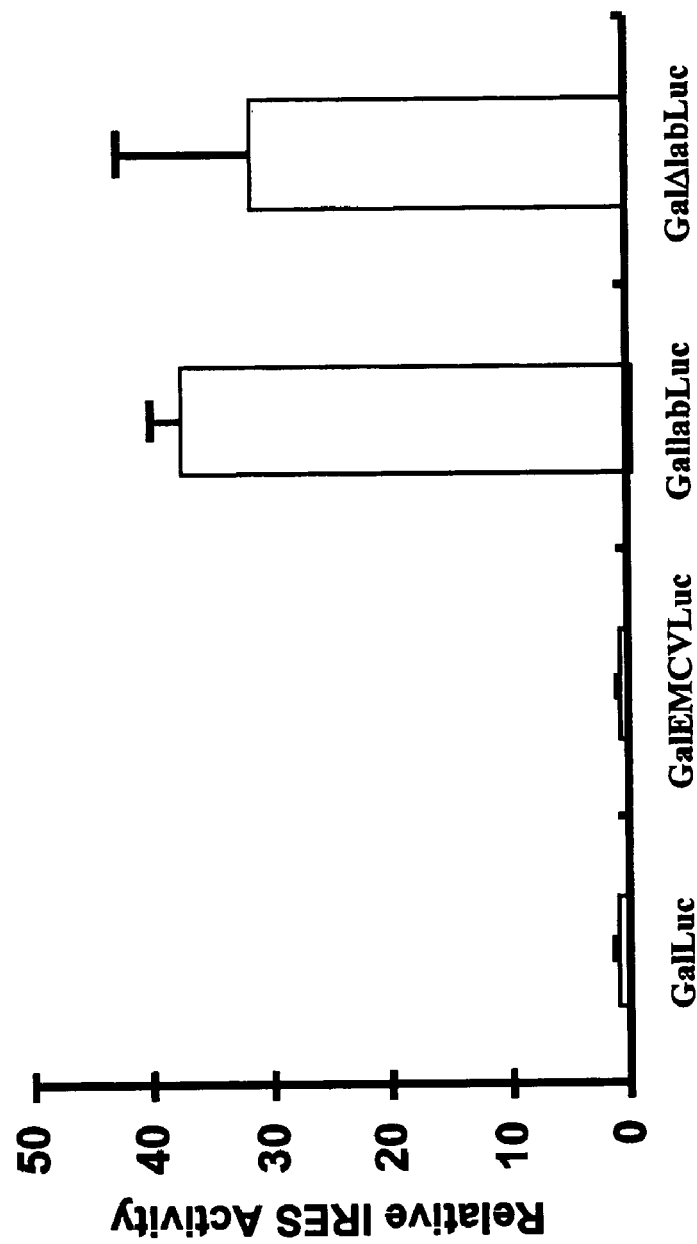

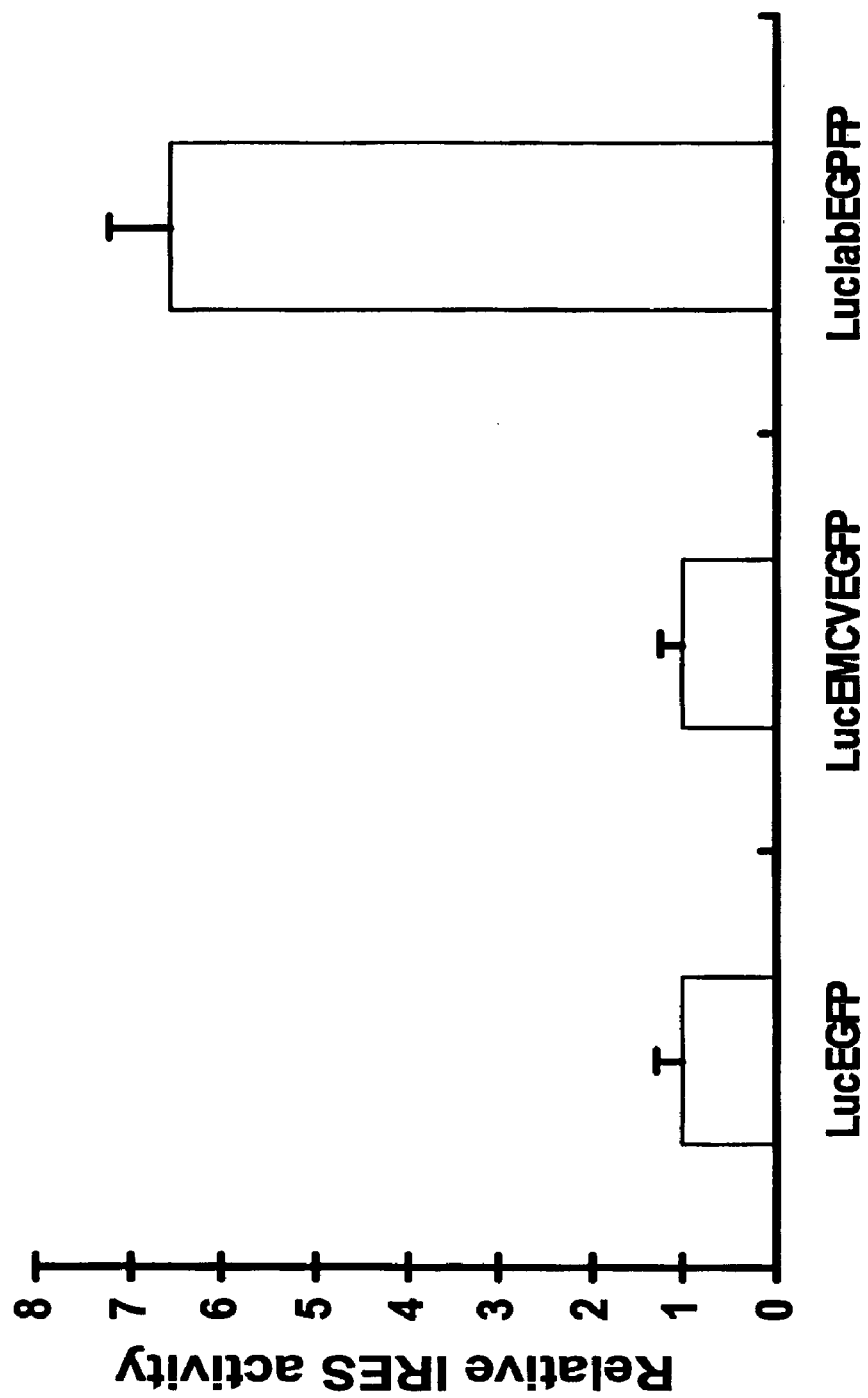

FIG. 10
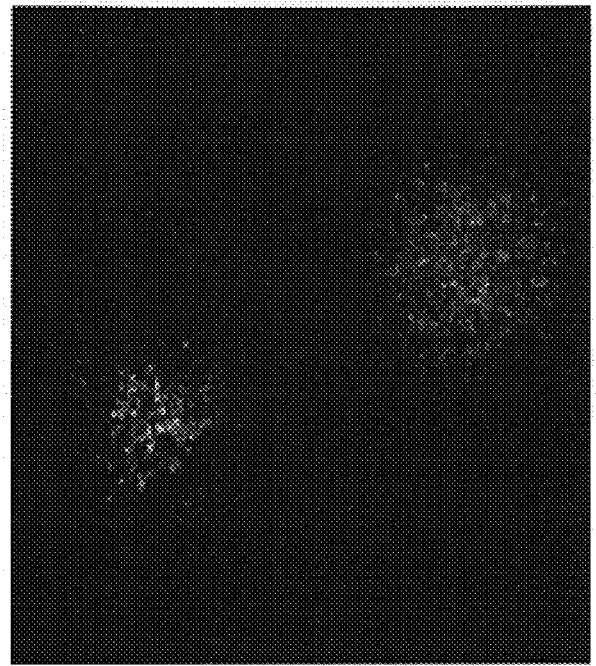

INTERNAL RIBOSOME ENTRY SITE OF THE LABIAL GENE FOR PROTEIN EXPRESSION

This application claims the benefit of U.S. Provisional Application No. 60/394,270, filed Jul. 9, 2002, the contents of which are relied on are incorporated herein by reference.

FIELD OF THE INVENTION

The present invention relates to the 5' untranslated region (5'UTR) of the *Drosophila labial* (lab) gene, which has a predicted stable secondary hairpin structure and functions as an internal ribosome entry site (IRES). The present invention further relates to methods of using the lab IRES in protein expression systems, to compositions comprising the lab IRES, and to homologs of the lab IRES.

BACKGROUND OF THE INVENTION

The *Drosophila* undergoes a complete metamorphosis in its progression from an embryo to an adult. The embryo is characterized by its polarity, which readily distinguishes the anterior and posterior, dorsal and ventral parts of the animal, and by serially repeating segments (or metameres), each with characteristic structural patterns. The adult body is also segmented, and groups of these segments are organized into a head, thorax, and abdomen.

Three major classes of pattern-regulating genes specify the basic features of the *Drosophila* embryo's body and function in successive states of development. The maternal genes are expressed in the unfertilized egg and provide most of the proteins needed in very early development. The maternal genes direct the spatial organization of the developing embryo at early stages, establishing its polarity. The segmentation genes are expressed after fertilization and direct the formation of the proper number of body segments. Finally, the homeotic genes are expressed later and affect the unique characteristics of the individual body segments.

In general, the homeotic genes control the fundamental architectural plan of the embryo. The two main clusters of homeotic genes found in the *Drosophila* genome are the Antennapedia complex (ANT-C) and the Bithorax complex (BX-C). The ANT-C directs the proper development of the head and anterior thoracic segments during fruitfly development and comprises five homeotic genes in the following sequential order: *labial* (lab), proboscipedia (pb), Deformed (Dfd), Sex combs reduced (Scr), and Antennapedia (Antp). The BX-C directs the proper development of the posterior thoracic segments and abdominal segments and comprises three homeotic genes in the following sequential order: Ultrabithorax (Ubx), abdominal A (abdA), and Abdominal B (AbdB). All of these homeotic genes code for specific RNA polymerase II transcription factors which are required for DNA transcription. Thus, the homeotic genes regulate segment development and body plan formation by regulating DNA transcription.

The genetic order of the homeotic genes within the two complexes correlates with the sequence of metameres on which they act. Thus, the most proximate member of the ANT-C complex, the *labial* (lab) gene, is the most anteriorly expressed and is critical for the development of the embryonic and adult head. In contrast, the AbdB gene of the BX-C complex is the most posteriorly expressed homeotic gene and affects the formation of structures at the posterior end of the embryo or the adult fly. Thus, the functional specificity of the different homeotic genes is achieved partly by their precise spatial and temporal expression patterns.

It has been reported that two of the *Drosophila* homeotic genes, Antp and Ubx, are translated by a unique cap-independent mechanism in contrast to the cap-dependent mechanism utilized by most other eukaryotic genes. Eukaryotic mRNAs have a distinctive structural feature at its 5' end, called a 5' cap, which is a residue of 7-methylguanosine linked to the 5' terminal residue of the mRNA through an unusual 5', 5'-triphosphate linkage. Cap-dependent translation is initiated by the binding of the cap-binding protein complex eIF-4F to the 5' cap, which in turn facilitates the binding of the 43S ternary ribosomal subunit near or at the 5' cap region. The ribosome complex is purported to scan the mRNA from the 5' cap until it encounters the first AUG initiation codon, where translation of the mRNA is initiated. (see Kozak, M, (1989) *Cell* 44:283–292; Kozak, M (1989) *J. Cell. Biol.* 108:229–241).

The cap-independent translation mechanism was proposed to explain the efficient translation of some mRNAs despite the presence of a highly ordered RNA structure in the 5' untranslated region (5'UTR) of mRNAs which was predicted to interfere with ribosome scanning of the mRNA. The picornavirus mRNA was the first mRNA identified that displayed a cap-independent translation mechanism. The picornavirus mRNA is characterized by a unique structure, including the absence of a 5' cap, the presence of an extraordinarily long and structured 5' UTR, and the presence of multiple upstream AUG initiation codons. This long and structured 5'UTR was found to serve as an internal ribosome entry site (IRES) or a ribosome landing pad, where the 43S ternary ribosomal subunit would bind and initiate translation independently of the 5' cap structure.

The 5'UTR containing an IRES is generally characterized by three complex features: a long 5'UTR, a stable secondary structure, and potential upstream AUG initiation codons. The stable secondary structure is considered to be the major determinant of IRES function. A low proportion of vertebrate mRNAs have long, highly structured 5'UTRs that contain multiple AUG initiation codons. Among these, the *Drosophila* Antp gene has been found to harbor a 1,735 nt-long 5'UTR and 15 upstream AUG codons, and the Ubx gene has a 968 nt-long 5'UTR and two upstream AUG codons. To date, a limited, but a growing subset of IRESs have been identified in cellular mRNAs in various species including human (Macajak, D. G. and P. Sarnow, (1991) *Nature* 353:653–656; Sarnow, P, (1989) *PNAS* 86:5795–5799; Vagner, S. et al., (1995) *Mol. Cell. Biol.* 15:35–44), and yeast (Zhou, W. et al., (2001) *PNAS* 98:1531–1536; Paz, I. et al., (1999) *J. Biol. Chem.* 274: 21741–21745). IRESs have also been identified in viral mRNAs, such as in poliovirus (Pelletier, J. and N. Sonenberg. (1988) *Nature* 334:320–325), encephalomyocarditis virus (EMCV) (Jang, S. K., and E. Wimmer, (1990) *Genes Dev.* 4:1560–1572), and human rhinovirus (HRV) (Borman, A. et al., (1993) *J. Gen. Virol.* 74:1775–1788). The Antp and Ubx homeotic genes of *Drosophila* are also translated via an IRES in their long 5'UTRs (Ye X. et al., (1997) *Mol. Cell. Biol.* 17:1714–1721; Ho, S.-K. et al., (1992) *Genes Dev.* 6:1643–1653).

THE INVENTION

The present invention provides an internal ribosomal entry site (IRES) from the 5' UTR of the *Drosophila* lab gene. The lab IRES directs the cap-independent translation of mRNA. Thus, the lab IRES is useful in nucleic acid vectors to direct the expression of two or more unrelated proteins from a single transcriptional unit.

Conventionally, a recombinant protein is expressed in a cell by placing its gene under the control of a promoter, which provides the RNA polymerase binding site necessary for mRNA synthesis. When two or more recombinant proteins are to be expressed in a cell, each of their genes is placed under the control of separate promoters in a single nucleic acid vector. Alternatively, each of the proteins may be expressed from separate nucleic acid vectors. In either method, a separate mRNA transcript is generated for each protein. Translation of different mRNA transcripts often leads to the uncoupled expression of the various proteins. If multiple proteins are placed under the control of a single promoter, it has been observed that the first gene most proximal to the 5' cap is most efficiently translated, presumably by the cap-dependent process, while the downstream genes may be translated at low levels or not at all. However, when an IRES is inserted into a nucleic acid vector between genes downstream of the 5' most proximal gene, two or more proteins may be efficiently translated from a single mRNA transcript.

The nucleic acid vector directing the expression of more than one protein from a single vector is known in the art as a multicistronic vector. In a multicistronic vector, a nucleotide sequence comprising at least two cistrons, or genes, is placed under the control of a promoter for mRNA synthesis, and an IRES is inserted between two cistrons. A single mRNA transcript is generated containing sequences of the first cistron, IRESs, and other downstream cistrons, rather than separate mRNA transcripts as in the conventional approach. During translation, the first cistron is translated by the ribosomal scanning mechanism because it is most proximal to the 5' cap while the second cistron and other downstream cistrons are translated by internal ribosome binding to the IRES. As a result, a constant ratio of mRNAs expressing multiple cistrons is maintained. The major advantage of this technique is the co-expression of two or more proteins from a single mRNA, avoiding the use of separate expression constructs and multiple promoters which often leads to uncoupled expression of the proteins.

The lab IRES of the present invention can direct such cap-independent translation in a wide range of cell types, including insect and mammalian cells. This is quite advantageous because the baculovirus expression system is widely applicable as an alternative to prokaryotic or other eukaryotic expression systems for the high level production of recombinant proteins. Many biologically active proteins have been produced at high levels using the baculovirus system (for review see Miller, L. K., (1988) *Annu. Rev. Microbiol.* 42:177–199; Luckow V. A. and M. D. Summers, (1988) *Bio/Technology* 6:47–55; Luckow V. A., (1990) In: *Recombinant DNA Technology and Applications.* McGraw-Hill, New York, pp. 97–152; O'Reilly, D. R., et al., (1992) *Baculovirus Nucleic acid vectors: A Laboratory Manual*, W. H. Freedman, New York). In the baculovirus system, the baculovirus polyhedrin gene is usually replaced with the gene encoding for the protein of interest. The polyhedrin gene is highly expressed in infected insect cells but is not essential for viral propagation, and is therefore the ideal location to place the gene of interest. This segment of the baculovirus gene is placed in a separate transfer vector and under the control of the strong polyhedrin promoter. This transfer vector is co-transfected into baculovirus host cells with a baculovirus genomic DNA. Recombinant baculoviruses carrying the gene of interest is produced when homologous recombination between the transfer vector and baculovirus genomic DNA occurs. These recombinant baculoviruses are used to infect host cells, which will produce large amounts of the desired protein.

However, despite the attractiveness of the baculovirus expression system, other IRESs have not been shown to be active in baculovirus host cells. Thus, while the encephalomyocarditis virus (EMCV) IRES element is known to be highly efficient in mammalian systems, it does not promote efficient internal translation in various baculovirus host insect cells, presumably because the insect cells do not have the cellular factors required to initiate internal translation that are present in mammalian cells (Finkelstein Y., et al., (1999) *J. Biotech.* 75:33–44).

It would therefore be desirable to identify a novel IRES that functions in baculovirus host insect cells as well as in other cell types. The use of IRESs in recombinant protein expression systems, such as the baculovirus system, would allow the expression of two or more proteins from a single mRNA template. Moreover, the expression of a gene of interest and a reporter gene would also allow the simultaneous evaluation of recombinant protein level produced and the detection/isolation of cells producing high levels of the recombinant protein. Recombinant proteins produced by these methods may also be useful as therapeutic agents. The nucleic acid vectors may additionally be useful for gene therapy.

The present invention also provides homologs, fragments, and variants of the lab IRES, as well as variants and fragments of homologs of the lab IRES. The present invention further provides multicistronic nucleic acid vectors comprising the lab IRES or a homolog, fragment, or variant thereof having IRES activity, for the production of multiple recombinant proteins from a single mRNA transcript. These multicistronic nucleic acid vectors may be contained in a biological vector capable of expressing multiple genes in a host cell. These nucleic acid vectors and biological vectors may be used for the genetic treatment in patients and/or the recombinant proteins produced thereby may be useful as therapeutic agents.

The present invention also provides a baculovirus transfer vector and a recombinant baculovirus for the expression of at least two genes in a baculovirus host cell, comprising a lab IRES or a homolog, variant, or a fragment thereof having IRES activity. The ability to express two or more genes from a single baculovirus transfer vector and a recombinant baculovirus greatly simplifies the process of isolating plaques expressing the gene(s) of interest. Moreover, the expression of two genes permits the expression of a gene of interest and a reporter gene. This allows the simultaneous evaluation of recombinant protein level produced and the detection/isolation of cells producing high levels of the recombinant protein.

BRIEF DESCRIPTION OF THE DRAWINGS

FIG. 1 FIG. 1 illustrates the structure of the lab gene 5'UTR. FIG. 1A shows the nucleotide sequence (SEQ ID NO:1) and FIG. 1B shows the predicted Y-shaped secondary structure of the lab 5' UTR.

FIG. 2 FIG. 2 illustrates the bicistronic vectors and assays used for determining IRES activity of the lab 5'UTR. FIG. 2F shows the cell cycle arrest of Drosophila Kc cells in the G2/M phase after treatment with colcemid. The second peak at around 600 nm represents cells in the G2/M phase. FIG. 2H shows the bicistronic vectors containing the β-galactosidase and luciferase genes under the control of the Drosophila cyclin B1 promoter (cycB). EMCV and Lab represent IRES sequences inserted between the β-galactosidase and luciferase genes. The bottom panel shows the relative IRES activities of the bicistronic vectors pCycBGalLuc, pCycBGalEMCVLuc, and pCycBGalLabLuc during the G2/M phase of Drosophila Kc cells.

FIG. 3 FIG. 3 shows the relative IRES activities in Drosophila S2 cells transfected with the bicistronic vectors pAcGalLuc, pAcGalAntpLuc, pAcGalUbxLuc, pGalNluc, and pAcGalLabLuc. Antp represents the Drosophila Antennapedia IRES, Ubx represents the Drosophila Ultrabithorax IRES, N represents the 5'UTR of the Notch protein, and Lab represents the Drosophila lab 5'UTR.

FIG. 4 FIG. 4 illustrates the structure of the 5'UTR of the human Homeobox A1. FIG. 4A shows the nucleotide sequence of Homeobox A1 (SEQ ID NO: 2) compared with that of the lab 5'UTR (residues 1–238 of SEQ ID NO: 1) and the consensus sequence of lab IRES homologs. FIG. 4B shows the predicted Y-shaped secondary structure of the Homeobox A1 5' UTR.

FIG. 5 FIG. 5 illustrates IRES activity of the Homeobox A1 5'UTR.

FIG. 6 FIG. 6 illustrates the various modifications made in the lab and Homeobox A1 5'UTRs and their respective IRES activities.

FIG. 8 FIG. 8 illustrates IRES activity of the lab IRES in baculovirus host cells. FIG. 8A is a schematic representation of the bicistronic nucleic acid vectors pOpIE2GalLuc, pOpIE2GalEMCVLuc, pOpIE2GallabLuc, and pOpIE2GalΔlabLuc used to transfect the baculovirus host cells Sf9, Sf21, and High Five™ cells. OpIE2 represents the Orgyia pseudotsugata multicapsid nucleopolyhedrosisvirus immediate-early 2 promoter and Δlab represents nucleotides 1–215 of the lab IRES, which lacks domain III of the full-length lab IRES. FIGS. 8B, 8C, and 8D show the relative IRES activities of the four bicistronic vectors in Sf9 cells, Sf21 cells, and High Five™ cells, respectively.

FIG. 9 FIG. 9 illustrates the use of the lab IRES in a baculovirus expression system. FIG. 9B shows the relative IRES activity in Sf21 cells infected with recombinant baculoviruses generated from the bicistronic vectors pPolhLucEGFP (control), pPoIhLucEMCVEGFP, and pPolhLuclabEGFP.

FIG. 10 FIG. 10 illustrates the use of the lab IRES in a baculovirus plaque assay. The top panel is a schematic representation of the bicistronic vector pPolhLuclabEGFP. The bottom panel shows plaques of Sf21 cells infected with recombinant baculovirus generated from the bicistronic vector expressing both the β-galactosidase and the *luciferase* genes.

DETAILED DESCRIPTION OF THE INVENTION

Figure 2A:
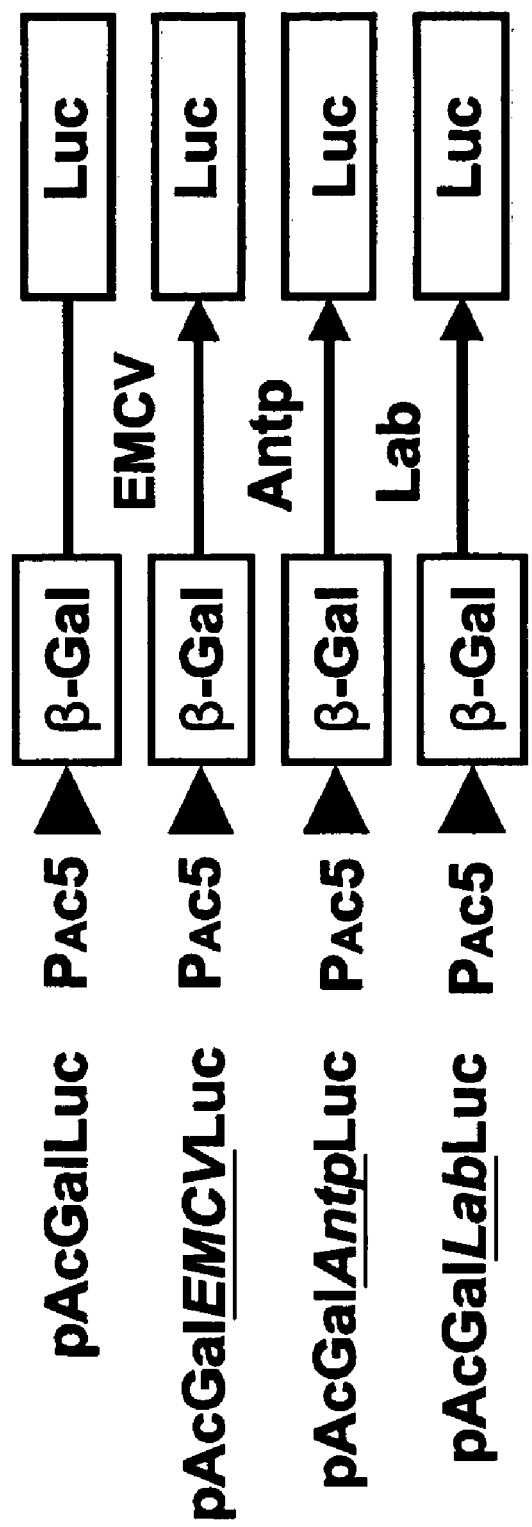
FIG. 2A is a schematic representation of the bicistronic nucleic acid vectors containing the β-galactosidase gene (Gal) and the firefly luciferase gene (Luc) under the control of the *Drosophila* Actin 5C promoter (Ac). EMCV, Antp, and Lab represent the IRES sequences inserted between the β-galactosidase and luciferase genes.

The present invention provides an isolated nucleotide sequence or cDNA of the internal ribosome entry site (IRES) in the Drosophila labial (lab) 5'UTR region. The 5' untranslated region (UTR) of the Drosophila lab gene is 293 nucleotides in length and is set forth in SEQ ID NO:1 and in FIG. 1A. Using Zuker's RNA folding program (Zuker, M., (1989) Methods Enzymol. 108:262–288) the 5'UTR of the lab mRNA is predicted to fold into a Y-type stem-loop structure comprised of three highly stable stem-loop domains: domain 1 (nucleotides 1–44), domain II (nucleotides 45–215), and domain III (nucleotide 216–239) (FIG. 1B). A nucleotide sequence or cDNA of the invention may be isolated by any technique known in the art, for example, by cloning using suitable probes, by the polymerase chain reaction (PCR), or alternatively, by chemical synthesis. As shown hereinbelow, the 5'UTR of the lab gene exhibits IRES activity.

As used herein, "IRES activity" refers to cap-independent translation initiated by internal ribosome binding, as opposed to cap-dependent translation. "Cap-dependent translation" refers to the mechanism of translation in which the ribosomal unit essential for initiating translation binds to mRNA at or near the 5' cap region on the mRNA. Cap-dependent translation is purported to proceed by a "ribosome scanning" mechanism whereby the ribosome complex scans the mRNA from the 5' cap until it encounters an AUG initiation codon. "Cap-independent translation" refers to the mechanism of translation in which the ribosomal unit essential for initiating translation binds to a site on the mRNA without requiring the 5' cap region. As used herein, the "IRES" is a nucleotide sequence that provides a site for ribosomal binding for cap-independent translation.

The present invention also relates to homologs, variants, or fragments of the lab IRES.

Figure 4A:
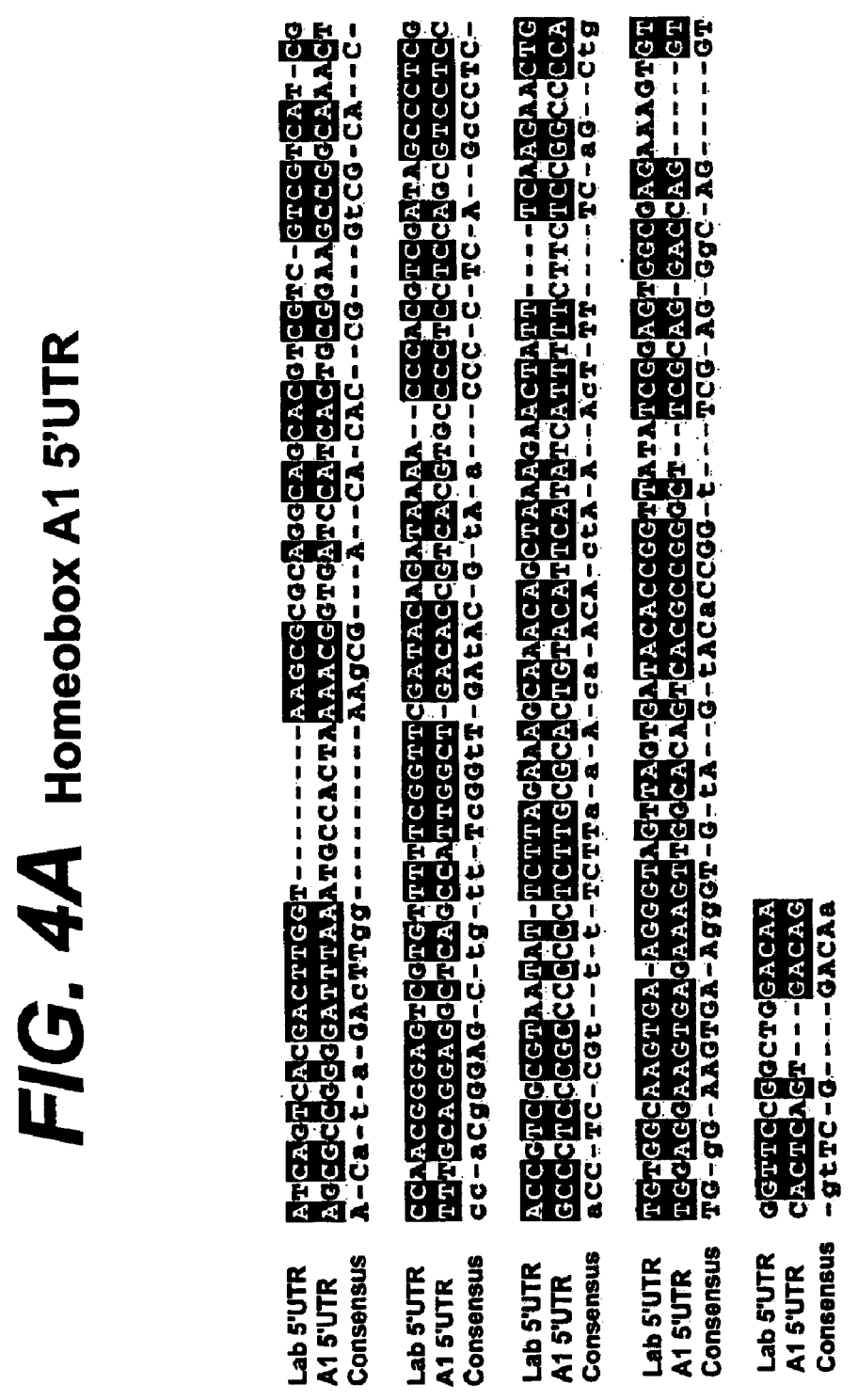

As used herein, "homolog" refers to structures or processes in different organisms that show a fundamental similarity. A homolog of the lab gene may play a functional role similar to that of the lab gene, i.e., in head development by regulating transcription in cells. A homolog of the lab gene may also have a primary or secondary structure similar to the lab gene. A homolog of the lab gene may also express gene products having homologous structures with the lab gene product, although their functions may differ widely. Similarly, a homolog of the lab IRES may have a primary or secondary structure similar to the lab IRES, and/or have IRES activity. FIG. 4A provides a consensus sequence of a lab IRES homolog. The present invention also includes variants and fragments of homologs of the lab IRES.

As used herein, "variant" of lab IRES refers a naturally-occurring or synthetically produced nucleotide sequence substantially identical to that of the lab IRES, but which has a nucleotide sequence different from that of the lab IRES because of one or more deletions, substitutions, or insertions. A variant of lab IRES retains IRES activity or has enhanced IRES activity compared with the lab IRES.

As used herein, "fragment" of lab IRES refers to a portion of the IRES nucleotide sequence that comprises less than the complete IRES nucleotide sequence and that retains essentially the same or exhibits enhanced IRES activity as the complete IRES nucleotide sequence.

Sequence "similarity" and/or "identity" are used herein to describe the degree of relatedness between two polynucleotides or polypeptide sequences. In general, "identity" means the exact match-up of two or more nucleotide sequences or two or more amino acid sequences, where the nucleotide or amino acids being compared are the same. Also, in general, "similarity" means the exact match-up of two or more nucleotide sequences or two or more amino acid sequences, where the nucleotide or amino acids being compared are either the same or possess similar chemical and/or physical properties. The percent identity or similarity can be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). Other programs for calculating identity and similarity between two sequences are known in the art.

For purposes of the invention, a homolog, variant, or fragment of the lab IRES may exhibit at least about 20% nucleotide identity with the lab IRES, at least about 30% nucleotide identity, or at least about 40% nucleotide identity, although the invention certainly encompasses sequences that exhibit at least about 50%, 60%, 70%, 80% and 90% nucleotide identity with lab IRES. Furthermore, a homolog, variant, or fragment of the lab IRES may exhibit a similar range of nucleotide sequence similarity with the lab IRES, from at least about 50%, 60%, 70%, 80%, and 90% nucleotide sequence similarity. Similarly, variants or fragments of the lab IRES homolog may exhibit a nucleotide identity with the lab IRES homolog of at least about 20% up to at least about 90% in increments of 10 as above, or a nucleotide similarity with the lab IRES homolog of at least about 50% to at least about 90%, in increments of 10 as above. Naturally-occurring homologs, variants, and fragments are encompassed by the invention.

Homologs, variants, or fragments of lab IRES may be obtained by mutation of nucleotide sequences of the lab IRES, following techniques that are routine in the art. Mutations may be introduced at particular locations by synthesizing oligonucleotides containing a mutant sequence, flanked by restriction sites enabling ligation to fragments of the native sequence. Following ligation, the resulting reconstructed sequence contains the desired insertion, substitution, or deletion. See Sambrook et al., *Molecular Cloning: A Laboratory Manual*, Vols 1–3 (2d ed. 1989), Cold Spring Harbor Laboratory Press.

Alternatively, oligonucleotide-directed site-specific mutagenesis procedures may be employed to provide an altered nucleotide sequence wherein predetermined sequences may be altered by substitution, deletion or insertion. Exemplary methods of making the alterations set forth above are known in the art (Walder R. Y. et al., (1986) *Gene* 42:133–139; Bauer C. E., et al., (1985) *Gene* 37:73–81; Craik C. S., (January 1985) *BioTechniques*, 12–19; Smith et al., (1981) *Genetic Engineering: Principles and Methods*, Plenum Press; Kunkel T. A., (1985) *Proc. Natl. Acad. Sci. USA* 82:488–492; Kunkel T. A., et al., (1987) *Methods in Enzymol*. 154:367–382; U.S. Pat. Nos. 4,518,584 and 4,737,462, all of which are incorporated by reference). Other methods known in the art may also be used.

The IRES of the invention may comprise one, two, or all three domains of the Y-type stem loop structure, including homologs or variants thereof, as discussed above. In an embodiment, the lab IRES comprises domains I and II of the 5' UTR of the lab gene, or homologs or variants thereof.

The IRES of the invention may also comprise one or more binding sites for a translational repressor such as the polyprimidine tract binding protein (PTB) which is disrupted by one or more deletions, substitutions, or additions in the nucleic acid sequence of the repressor binding site. The IRES activity is maintained or enhanced due to the disruption of the translational repressor binding site.

IRES activity may be determined by its ability to translate mRNA independently of the 5' cap region of the mRNA. Several reports support the hypothesis that IRES activity is cell type-dependent (Oumard A., et al., (2000) *Mol. Cell. Biol*. 20:2755–2759; Stoneley M., et al., (1998) *Oncogene* 16:423–428; Pozner A., et al., (2000) *Mol. Cell. Biol*. 20:2297–2307). These reports suggested that IRES activity is dependent on interaction with specific protein factors present in different cells.

The lab IRES or a homolog, variant, or fragment thereof of the present invention is capable of directing cap-independent translation in *Drosophila* cells and/or mammalian cells. The lab IRES or a homolog, variant, or fragment thereof of the present invention may also have this IRES activity in other eukaryotic cells, such as yeast, plants, and other insect cells.

The present invention further encompasses DNA constructs comprising the lab IRES or a homolog, variant, or fragment thereof, such as plasmids and recombinant expression vectors. In recombinant expression vectors, the lab IRES or a homolog, variant, or fragment thereof directs the expression of at least one recombinant protein. The construction and expression of conventional recombinant nucleic acid vectors is well known in the art and includes those techniques contained in Sambrook et al., *Molecular Cloning: A Laboratory Manual*, Vols 1–3 (2d ed. 1989), Cold Spring Harbor Laboratory Press. Such nucleic acid vectors may be contained in a biological vector such as viruses and bacteria, preferably in a non-pathogenic or attenuated microorganism, including attenuated viruses, bacteria, parasites, and virus-like particles.

In the context of the present invention, the isolated nucleotide sequence of the lab IRES or a homolog, variant, or fragment thereof is positioned upstream of a gene, or cistron, of interest in the nucleic acid vector in order to direct the cap-independent translation of an expression product. A variant or fragment of a lab IRES homolog may also be used. The nucleic acid vector may be of the monocistronic type (for the expression of a single gene of interest under the control of a promoter for mRNA synthesis) or of the multicistronic type (for the expression of at least two genes of interest placed under the control of the same promoter for mRNA synthesis). Such a nucleic acid vector may contain several "IRES-cistron" elements in tandem, wherein at least one of the IRES sites comprises the nucleotide sequence of the lab IRES or a homolog, variant, or fragment thereof, or alternatively, a variant or fragment of a lab IRES homolog.

The nucleic acid vectors of the present invention comprise a promoter operably linked to a nucleotide sequence comprising at least one cistron operably linked to an isolated nucleotide sequence of a lab IRES or a homolog, variant, or fragment thereof, or a variant or fragment of a lab IRES homolog. A promoter is required for mRNA synthesis from a DNA sequence and an mRNA with a 5' cap is usually synthesized in eukaryotes. As used herein, "cistron" refers to a polynucleotide sequence, or gene, of a protein, polypeptide, or peptide of interest. "Operably linked" refers to a situation where the components described are in a relationship permitting them to function in their intended manner. Thus, for example, a promoter "operably linked" to a cistron is ligated in such a manner that expression of the cistron is achieved under conditions compatible with the promoter. The nucleic acid vector may further comprise one or more additional "IRES-cistron" elements in tandem.

Cistrons may include genes coding for receptors, ion channels, subunits of proteins, enzymes, antibodies, protein ligands, proteins conferring antibiotic resistance to cells, growth factors, hormones, or any other proteins, polypeptides, or peptides of interest. In one embodiment of the present invention, at least one cistron in the nucleic acid vector of the present invention comprises a therapeutic gene coding for a therapeutic agent capable of inhibiting or delaying the establishment and/or development of a genetic or acquired disorder, such as cystic fibrosis, hemophilia A or B, Duchenne or Becker type myopathy, cancer, AIDS and other bacteria or infectious diseases due to a pathogenic organism. Examples of such therapeutic agents include, but are not limited to: a cytokine; interleukin; interferon; a factor or cofactor involved in coagulation, such as factor VIII, factor IX, von Willebrand factor, antithrombin III, protein C, thrombin, and hirudin; enzyme inhibitors such as viral protease inhibitors; an ion channel activator or inhibitor; a protein capable of inhibiting the initiation or progression of cancers, such as expression products of tumor suppressing genes (p53, Rb genes, etc.), a toxin, an antibody, or an immunotoxin; or a protein capable of inhibiting a viral infection or its development, for example, an antigenic epitope of the virus in question, an antibody or an altered variant of a protein capable of competing with the native viral protein.

In another embodiment of the present invention, at least one cistron in the nucleic acid vector of the present invention comprises a reporter gene, for example, a gene coding for β-galactosidase, firefly luciferase, green fluorescent protein, or the red fluorescent protein from Discosoma sp. (DsRed). Other reporter genes known in the art may be used. Reporter genes facilitate the detection of cells expressing a functional protein from a nucleic acid vector. Detection of reporter proteins may be made by providing a substrate required for the enzymatic reaction producing a readily detectable product by eye, luminescence, fluorescence, or microscopy. Other reporter gene products, such as the green fluorescent protein, may be observed directly under the microscope under appropriate fluorescent or luminating conditions.

Promoters that may be sued in the invention include viral promoters and cellular promoters and are well known in the art. Viral promoters may include the cytomegalovirus (CMV) promoter, the baculovirus polyhedrin promoter, the major late promoter from adenovirus 2 and the SV40 promoter. Examples of cellular promoters include the *Drosophila* actin 5C distal promoter and the mouse metallothionein 1 promoter. Other promoters useful for the nucleic acid vectors of the present invention may be readily determined by those skilled in the art.

Also contained in nucleic acid vectors is a polyadenylation signal located downstream of the last cistron of interest. Polyadenylation signals include the early or late polyadenylation signals from SV40, adenovirus 5 E1B, and the human growth hormone gene. The nucleic acid vectors may also include an enhancer sequence, such as the SV40 and CMV enhancer.

In order to identify cells that have acquired the nucleic acid vector, a selectable marker is generally introduced into the cells along with the gene of interest. Selectable markers include genes that confer drug resistance to the cells, such as ampicillin, neomycin, hygromycin and methotrexate. Selectable markers are reviewed by Thilly (Mammalian Cell Technology, Butterworth Publishers, Stoneham, Mass.) and the choice of selectable markers is well within the level of ordinary skill in the art.

Selectable markers may be introduced into the cell on a separate plasmid at the same time as the nucleic acid vector or they may be on the same nucleic acid vector. If on the same nucleic acid vector, the selectable marker and gene(s) of interest may be under the control of different promoters or IRESs or the same promoter or IRES.

If it is desired that the gene product of interest be secreted from the cell, a secretory signal sequence may be placed immediately upstream of and in-frame of the gene of interest in the nucleic acid vector. Many secretory signal sequences are known in the art, such as the signal sequences of human serum albumin, human growth factor, the alpha factor signal sequence, and the immunoglobulin chains, to name a few. Alternatively, secretory signal sequences may be synthesized according to the rules established, for example, by von Heinje (*Eur. J. Biochem.* 13: 17–21, 1983; *J. Mol. Biol.* 184:99–105, 1985; *Nuc. Acids Res.* 14:4683–4690, 1986).

The present invention also encompasses methods for expressing at least one cistron of interest comprising introducing into a host cell a nucleic acid vector comprising a promoter operably linked to a nucleotide sequence comprising at least one cistron operably linked to a nucleotide sequence of a lab IRES or a homolog, variant, or fragment thereof, or a variant or fragment of a lab IRES homolog. The nucleic acid vector may further comprise one or more additional "IRES-cistron" elements in tandem for expression of at least two cistrons.

The nucleic acid vectors may be introduced into cultured host cells by, for example, calcium phosphate-mediated transfection (Wigler et al., (1978) *Cell* 14:725; Corsaro and Pearson (1981) *Somatic Cell Genetics* 7:603; Graham and Van der Eb. (1973) *Virology* 52:456). Other techniques for introducing nucleic acid vectors into host cells, such as electroporation (Neumann et al., (1982) *EMBO J.* 1:841–845), may also be used.

Transfected cells are allowed to grow for a period of time to allow the expression of the gene(s) of interest. Drug selection may be applied to select for growth of cells expressing the selectable marker. Host cells containing the nucleic acid vectors of the present invention are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals and growth factors. The growth medium may also include a drug to select for cells expressing a selectable marker from the introduced nucleic acid vector.

A stable cell line may be established when the cells have been selected for stable integration of the gene of interest into the host genome. Usually, stable cell lines are established after having undergone drug selection for about three days to about three weeks.

As described above, the nucleic acid vector of the present invention may be contained in a biological vector such as viruses and bacteria, preferably in a non-pathogenic or attenuated microorganism, including attenuated viruses, bacteria, parasites, and virus-like particles. Examples of such biological vectors include poxvirus (e.g. vaccinia virus); adenovirus; baculovirus; herpesvirus, adeno-associated virus, and retrovirus. Such vectors are amply described in the literature. In an embodiment of the present invention, the nucleic acid vector of the present invention may be contained in a recombinant baculovirus capable of infecting a baculovirus host cell and expressing a gene of interest. The baculovirus expression system is described in the art, for example, in U.S. Pat. Nos. 4,745,051, 4,879,236, and 5,147,788, Miller, L. K. (*Annu. Rev. Microbiol.* 42:177–199, 1988), Luckow, V. A. (In: *Recombinant DNA Technology and Applications*. McGraw-Hill, New York, pp. 97–152, 1990), and O'Reilly, D. R., et al. (*Baculovirus Nucleic acid vectors: A Laboratory Manual*, W. H. Freedman, New York, 1992), all of which are incorporated herein by reference.

In general, generation of recombinant baculoviruses capable of infecting a host cell and expressing a gene of interest involves the co-transfection of a recombinant transfer vector and a baculovirus genomic DNA into a baculovirus host cell. A recombinant baculovirus transfer vector is generally derived from a DNA fragment of the baculovirus genomic DNA comprising the polyhedrin promoter and polyhedrin gene. In a recombinant baculovirus transfer vector, a gene of interest is placed under the control of the polyhedrin promoter, replacing some or all of the sequences of the polyhedrin gene. A recombinant baculovirus transfer vector of the present invention comprises a polyhedrin promoter operably linked to a nucleotide sequence comprising at least one cistron operably linked to a nucleotide sequence of a lab IRES or a homolog, variant, or fragment thereof, or a variant or fragment of a lab IRES homolog. The recombinant baculovirus transfer vector of the present invention may further comprise one or more additional "IRES-cistron" elements. Upon transfection of the recombinant transfer vector and baculovirus genomic DNA into susceptible host cells, the recombinant transfer vector and baculovirus genomic DNA undergo homologous recombination, thereby incorporating the gene(s) of interest into the baculovirus genome. Recombinant baculoviruses capable of expressing the gene(s) of interest are released into the extracellular medium. However, because neither transfection nor homologus transfection is 100% efficient, the result will be a mixture of cells that produce recombinant baculoviruses and those that do not. Recombinant baculoviruses capable of expressing the gene(s) of interest in baculovirus host cells are thereafter selected by appropriate screening or genetic selection techniques.

One means of selecting the recombinant baculovirus utilizes the plaque assay method. Plaque assays are designed to produce distinct viral plaques in a monolayer of host cells under conditions where each plaque is the result of a cell being infected by a single virus. Plaques are generated by infecting baculovirus host cells with diluted medium from cells transfected with the recombinant transfer vector and baculovirus genomic DNA. Infected cells form plaques, which may be visualized by overlaying infected cells with agar or under a microscope. Viral plaques may be isolated and are evaluated for recombinant baculovirus capable of expressing a gene of interest.

Many screening methods are available in the art to confirm that plaques isolated from the cotransfection contain recombinant baculoviruses. Preferred methods detect the synthesis of the target protein, e.g. Western blotting, ELISA, or biochemical assays for the expressed protein. Southern blot analysis and PCR may also confirm that the target gene is present in the recombinant baculovirus genome.

The present invention also relates to the treatment of a patient, or for the benefit of a patient, by administration of a nucleic acid vector or biological vector in an amount sufficient to direct the expression of a desired gene(s) in a patient. Administration of the nucleic acid vector or biological vector may provide the expression of a desired gene(s) that is deficient or non-functional in a patient. The nucleic acid vector or biological vector may be directly administered to a patient, for example, by intravenous or intramuscular injection or by aerosolization into the lungs. Alternatively, an ex vivo gene therapy protocol may be adopted, which comprises excising cells or tissues from a patient, introducing the nucleic acid vector or biological vector into the excised cells or tissues, and reimplanting the cells or tissues into the patient (see, for example, Knoell D. L., et al., (1998) *Am. J. Health Syst. Pharm.* 55:899–904; Raymon H. K., et al., (1997) *Exp. Neurol.* 144:82–91; Culver K. W., et al., (1990) *Hum. Gene Ther.* 1:399–410; Kasid A., et al., (1990) *Proc. Natl. Acad. Sci. U.S.A.* 87:473–477). The nucleic acid vector or biological vector may be introduced into excised cells or tissues by transfection or infection, such as by the methods described above.

A patient is hereby defined as any person or non-human animal in need of a specific protein, polypeptide, or peptide, or to any subject for whom treatment may be beneficial, including humans and non-human animals. Such non-human animals to be treated include all domesticated and feral vertebrates. One of skill in the art will, of course, recognize that the choice of protein, peptide, or polypeptide will depend on the disease or condition to be treated in a particular system.

The present invention is illustrated by the following Examples, which are not intended to be limiting in any way.

EXAMPLE 1

Reagents and Assays for Determining IRES Activity

Cell Culture and Cell Transfection

*Drosophila* S2 cells were maintained at 23.5° C. in DES (Invitrogen) supplemented with 10% fetal bovine serum (Life Technologies). At 24 h before transfection, cells were plated at a density of $3\times10^6$ cells per well in a 6-well plate. Cells were transfected using calcium phosphate-mediated transfection (Clontech). After 16 h of incubation, the culture medium was replaced with fresh medium. 0.5 mM $CUSO_4$ was added to induce expression. At 60 h after transfection, cells were harvested and IRES activity was measured by using the β-Galatosidase and luciferase assay described below.

Baculovirus host cells *Sphodoptera frugiperda* (fall armyworm) Sf21 and Sf9 cells were maintained at 27° C. Grace's medium (Life Technologies) with 10% fetal bovine serum (Life Technologies). The commercially available baculovirus host cells from Invitrogen, High Five™ cells, were maintained at 27° C. in High Five™ cell culture medium. At 24 h before transfection, cells were plated at a density of $2\times10^5$ per well in a 6-well plate. Cells were transfected by using Cellfectin (Life Technologies). Just prior to transfection, the medium was replaced with fresh medium without serum and antibiotics. Five micrograms of supercoiled DNA was mixed with 20 μl of Cellfectin in a total volume of 100 μl and the mixture was incubated at room temperature for 30 min. The DNA-Cellfectin complex was then added dropwise to the cells. The cells were incubated at 27° C. After 6 h of incubation at 27° C., 3 ml of medium supplemented with 13.3% serum was added. Cells were harvested after 48 h after transfection and IRES activity was measured using the β-Galatosidase and luciferase assay described below.

β-Galatosidase and Luciferase Assays

*Drosophila* S2 cells were homogenized in 200 μl Luc-Cite buffer at 4° C. for 30 min. and centrifuged at 12000 rpm to remove non-lysed cell pellets. 30 μl of the supernatant was transferred to a cuvette containing 270 μl of ortho-nitrophenyl-β-galactopyranoside (ONPG) solution (1 mM ONPG in assay buffer), and incubated at 37° C. for 30 min. 500 μl $H_2O$ was added to the cuvette to stop the reaction. The relative β-galactosidase activity was measured using the Spectra Max Plus (Molecular Devices) at 420 nm.

The luciferase assay followed the procedure provided with the Packard Luciferase Assay Kit. Briefly, 100 μl of the homogenized supernatant from above was mixed with 100 μl of luciferase substrate buffer and allowed to react for 10 min. The luciferase activity was then measured using the Microplate Scintillation and Luminescence Counter (Packard).

EXAMPLE 2

Structure of the 5'UTR of the lab mRNA

The 5'UTR of the lab mRNA contains 239 nucleotides (FIG. 1A). The secondary structure of the 5'UTR was deduced using Zuker's RNA folding program (Zucker, M. (1989) Methods Enzymol. 108:262–288). FIG. 1B shows the predicted secondary structure, a Y-type stem-loop structure comprising three highly stable stem-loop domains: domain I (nucleotides 1–44), domain II (nucleotides 45–215), and domain III (nucleotide 216–239).

EXAMPLE 3

The lab 5'UTR Exhibits IRES Activity

A bicistronic expression system having two reporter genes, β-galactosidase (in the first cistron) and luciferase (in the second cistron), was used to measure IRES activity. Four bicistronic nucleic acid vectors were constructed (FIG. 2A). In pAcGalLuc, the β-galactosidase and luciferase genes were placed under the control of the actin 5C distal promoter for mRNA synthesis. No promoter or IRES sequences are inserted between the β-galactosidase and luciferase genes in pAcGalLuc. Therefore, it would be expected that the β-galactosidase gene would be expressed by the cap-dependent translation mechanism, whereas the luciferase gene may be expressed at low levels or may not be expressed at all. pAcGallabLuc is similar to pAcGalLuc, except that the lab 5'UTR was inserted between the two cistrons. Thus, it would be expected that the β-galactosidase would be expressed by the cap-dependent translation mechanism, and that the luciferase gene would be expressed by the cap-independent translation mechanism if the lab 5'UTR acts as an internal ribosome entry site (IRES). pAcGalAntpLuc served as a positive control, with the *Drosophila* Antp IRES element inserted between the two cistrons in pAcGalLuc. The Antp 5'UTR is a known IRES that is functional in *Drosophila* cells (Ho, S.-K., et al., (1992) *Genes Dev.* 6:1643–1653). pAcGalEMCVLuc contains the encephalomyocarditis (EMCV) IRES between the two cistrons in pAcGalLuc. The EMCV IRES is known to function in mammalian cells and was tested for IRES activity in *Drosophila* cells.

Figure 2B:
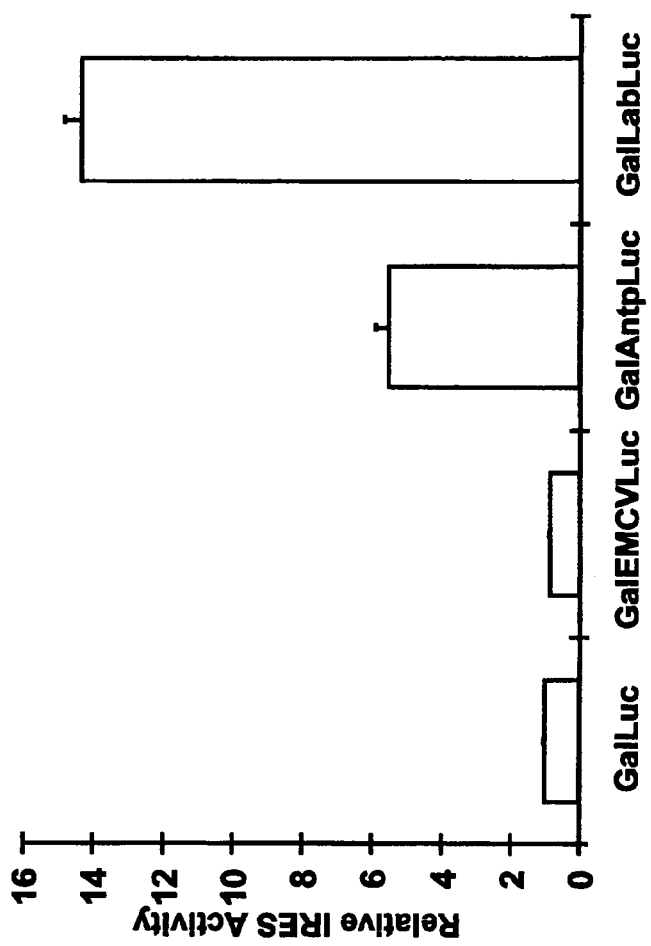
FIG. 2B shows the relative IRES activities of the four bistronic vectors pAcGalLuc, pAcGalEMCVLuc, pAcGalAntpLuc, and pAcGalLabLuc. IRES activity was calculated as ratios of luciferase activity to β-galactosidase activity from each bicistronic vector. Relative IRES activities were determined by normalizing each of the IRES activities to that of the control vector pAcGalLuc.

The four bicistronic plasmids (pAcGalLuc, pAcGalEMCVLuc, pAcGalAntpLuc, and pAcGallabLuc) were transfected into *Drosophila* S2 cells and assayed for β-galactosidase and luciferase activity at 72 h after transfection according to Example 1. It has been shown by others that the first (cap-dependent) cistron paralleled the steady-state level of the respective mRNA but was not significantly influenced by the protein coding sequence on the mRNA (Hennecke, M., et al., (2001) *Nucleic Acids Res.* 29:3327–3334). Therefore, translation from the cap-dependent cistron may be used as an internal standard to determine the strength of IRES-dependent translation of the second cistron. Thus, IRES activity may be defined by the ratio between the second (luciferase) cistron and the first (β-galactosidase) cistron. IRES activity of the four bicistronic plasmids was determined using this Luc/βGal ratio and the relative IRES activities were normalized to the Luc/βGal ratio of the control plasmid pAcGalLuc. As shown in FIG. 2B, the lab 5'UTR and Antp 5'UTR stimulated luciferase expression approximately 15-fold and 5-fold when compared to the control plasmid, pAcGalLuc. This experiment therefore demonstrates that the 5'UTRs of the two members of ANT-C complex, Antp and lab, exhibit IRES activity. In contrast, the EMCV IRES did not exhibit IRES activity in *Drosophila* S2 cells, despite the fact that it is known to exhibit strong IRES activity in mammalian cells (Creancier, L., et al., (2000) *Mol. Cell. Biol.* 21:1833–1840).

Figure 2C:
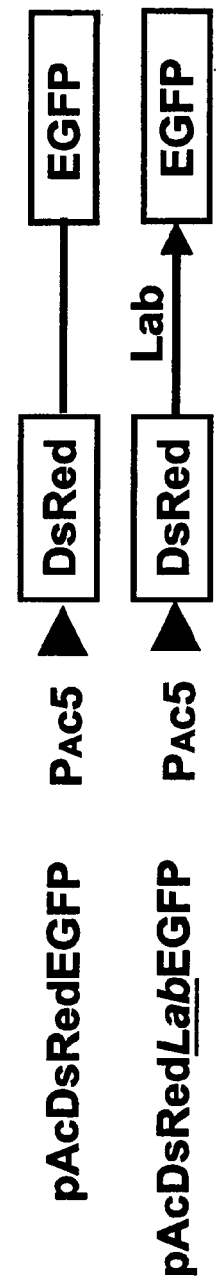
FIG. 2C is a schematic representation of the bicistronic vectors containing the DsRed fluorescent protein (DsRed) and the enhanced green fluorescent protein (EGFP) under the control of the actin 5C distal promoter (Ac). Lab represents the IRES sequence inserted between the DsRed and EGFP genes.
Figure 2D:
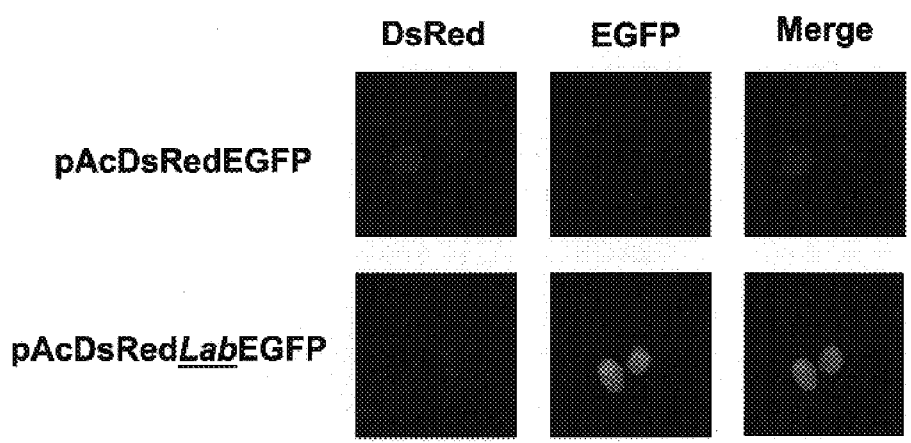
FIG. 2D shows the expression of the DsRed and EGFP proteins of Drosophila S2 cells transfected with either the pAcDsRedEGFP or pAcDsRedLabE-GFP constructs as analyzed by confocal microscopy.

The lab 5'UTR IRES activity was confirmed using a fluorescent bicistronic nucleic acid vector system (FIG. 2C). In pAcDsRedEGFP, the gene for the red fluorescent DsRed protein from Discosoma sp. and the gene for enhanced green fluorescent protein (EGFP) were placed under the control of the actin 5C distal promoter. Like pAcGalLuc above, no promoter or IRES sequences were inserted between the DsRed and EGFP genes. Therefore, it would be expected that the DsRed gene would be expressed by the cap-dependent translation mechanism, whereas the EGFP gene may be expressed at low levels or not expressed at all. The vector pAcDsRedLabEGFP contains an insertion of the 239 nt- lab 5'UTR between the DsRed gene (the first cistron) and the EGFP gene (the second cistron). The two bicistronic vectors were transfected into *Drosophila* S2 cells according to Example 1 and the cells were analyzed by confocal microscopy. As shown in FIG. 2D, cells transfected with pAcDsRedLabEGFP express both the DsRed and EGFP proteins in the same cell and the expression of EGFP from the lab IRES is significantly stronger than in cells transfected with the control vector, pAcDsRedEGFP.

Figure 2E:
FIG. 2E shows a northern blot analysis of the pAcGalLuc, pAcGalEMCVLuc, pAcGalAntpLuc, and pAcGalLabLuc transcripts hybridized with a β-galactosidase probe.

To rule out the possibility that increased expression from the lab IRES was caused by mRNA splicing, which may theoretically remove the first cistron and the lab IRES to bring the second cistron closer to the 5' cap region (and therefore become expressed by the cap-dependent translation mechanism), northern blot analysis was performed to ensure that the mRNAs of all four bicistronic nucleic acid vectors of FIG. 2A were of predicted sizes and hybridize with both the β-galactosidase and luciferase probes. FIG. 2E shows that all four bicistronic vectors produced mRNA transcripts of similar size and they all hybridized with both the β-galactosidase and luciferase probe (hybridization with a β-galactosidase probe shown). This confirms that the β-galactosidase and luciferase were translated from a single mRNA.

Further evidence that the lab 5' UTR contains IRES activity rather than cap-dependent translation activity was obtained from the observation that the lab 5'UTR is capable of mediating translation during the mitotic phase of the cell cycle (the G2/M phase), a phase during which cap-dependent translation is significantly reduced (Bonneau, A. M., and N. Sonenberg (1987) *J. Biol. Chem.* 262:11134–11139; Huang, J. T., and R. J. Scheider (1991) *Cell* 65:271–280). The loss of efficiency of cap-dependent translation is attributed to the fact that the cap binding protein, eIF-4E, which is an essential factor for initiating cap-dependent translation, becomes dephosphorylated during the mitotic phase and loses its ability to bind with the 5' cap structure. Consequently, genes carrying IRES elements have been shown to switch to a cap-independent translation mechanism during the G2/M phase.

Figure 2G:
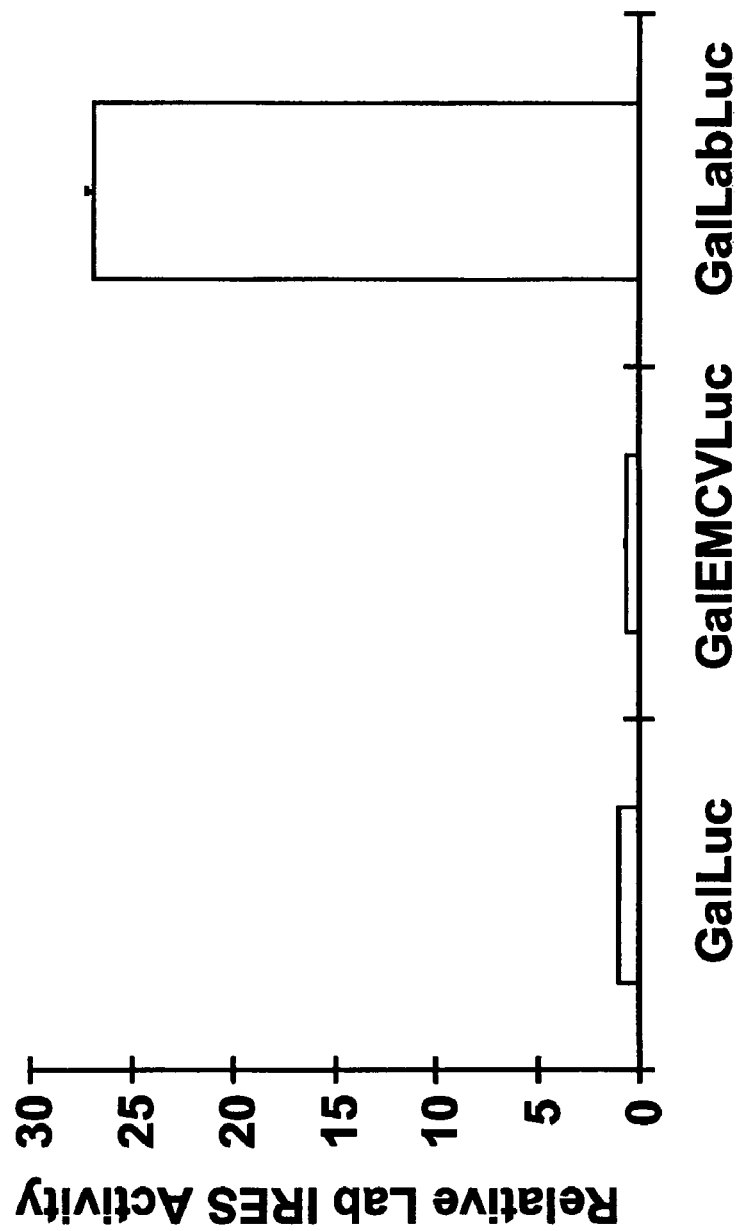
FIG. 2G shows the relative IRES activity of the bicistronic vectors pAcGalLuc, pAcGalEMCVLuc, and pAcGalLabLuc during the G2/M phase in Drosophila Kc cells.

To test whether the lab 5'UTR is capable of directing cap-independent translation during the G2/M phase, the bicistronic nucleic acid vectors pAcGalLuc, pAcGalEMCV-Luc, and pAcGallabLuc described above were transfected into *Drosophila* Kc cells according to Example 1. The transfected *Drosophila* Kc cells were treated with 10 µM colcemid (Sigma Chemical Co.) to arrest the cells in the G2/M phase. DNA content was measured by fixing cells in the presence of propidium iodide and subsequently analayzed by FACS analysis. FACS analysis revealed that the percentage of the cells in the G2/M phase increased from 20 to 30% (FIG. 2F, second peak at around 600 nm represents cells in the G2/M phase). When these Kc cells were measured for IRES activity using the Luc/βGal ratio described above, the lab IRES showed significant IRES activity during the G2/M phase (FIG. 2G).

To further confirm the observation that the lab IRES is active during the G2/M phase, the pCycBGalLuc bicistronic nucleic acid vector was used. The pCycBGalLuc control vector carries the *Drosophila* cyclin B1 promoter (CycB) which is upregulated to during the G2/M phase, resulting in an increased level of mRNA. CycB was placed upstream of the β-galactosidase gene for cap-dependent translation, and the EMCV or lab IRES elements were inserted between the first cistron (β-galactosidase) and the second cistron (luciferase) to test for IRES-dependent translation of the luciferase gene. The three bicistronic vectors, pCycBGalLuc, pCycGBalEMCVLuc, and pCycBGallabLuc were transfected into *Drosophila* Kc cells according to Example 1 and treated with colcemid. IRES activity was then determined using the Luc/βGal ratio described above. The lab IRES again exhibited IRES activity in the G2/M phase (FIG. 2H). These experiments confirm that the lab 5'UTR contains IRES activity and that the IRES is functional during the G2/M phase of the cell cycle when cap-dependent translation is not.

EXAMPLE 4

The lab IRES Exhibits the Strongest Activity when Compared with other Known and Unknown IRESs in *Drosophila* Cells The IRES activity of the lab gene was compared in *Drosophila* S2 cells with some known and unknown IRES candidates, including the 5'UTRs of the Antp, Ubx, and Notch (N) genes. Using the pAcGalLuc control vector described above in Example 3, each of the candidates were inserted between the β-galactosidase and luciferase cistrons to create pAcGalAntpLuc, pAcGalUbxLuc, pAcGalNLuc, and pAcGallabLuc. Each of the bicistronic nucleic acid vectors were transfected into *Drosophila* S2 cells according to Example 1 and IRES activity was measured according to Example 3. FIG. 3 shows that the lab IRES expressed the strongest luciferase activity, and therefore has the strongest IRES activity in *Drosophila* S2 cells.

EXAMPLE 5

The lab IRES Functions in a Wide Range of Cell Types

The lab IRES was analyzed for activity in other cell types, including the *Drosophila* Kc cell and the mammalian cell lines, HeLa, Cos-1, 293, and 3T3 cell lines. The bicistronic nucleic acid vector system was again used to test for IRES activity in these cells. For analysis in *Drosophila* Kc cells, the control vector pAcGalLuc described in Example 3 above was utilized. For analysis in the mammalian cell lines, that control vector was modified to place the β-galactosidase and luciferase genes under the control of the cytomegalovirus (CMV) promoter for mRNA synthesis because it is known to function in mammalian cells whereas the actin 5C distal promoter does not. This control vector used in mammalian cells was designated pCMVGalLuc. IRES sequences were inserted between the first and second cistrons to drive the IRES-dependent expression of the luciferase gene.

In *Drosophila* Kc cells, the lab IRES was compared with the Antp and EMCV IRESs. As described earlier, Antp IRES is known to function in *Drosophila* and the EMCV IRES is known to function in mammalian cells. As can be seen from Table 1 below, both Antp and lab IRESs had high IRES activity in *Drosophila* Kc cells, while the EMCV IRESs did not appear to exhibit any IRES activity.

In the mammalian cell lines HeLa, COS-1, 293, and 3T3 cells, lab IRES was compared with EMCV and hBip IRESs. The human immunoglobulin binding protein (hBip) 5'UTR has been identified as a mammalian cellular IRES (Macejak, D. G., and P. Sarnow (1991) *Nature* 353:90–94; Sarnow, P. (1989) PNAS 86:5795–5799). As described above, the EMCV IRES is known to function in mammalian cells.

Table 1 shows that lab IRES activity is comparable to that of hBip IRES in COS-1 and 3T3 cells but somewhat less active than hBip IRES in HeLa and 293 cells. Both hBip and lab IRESs were 3–6 fold lower in activity than that of EMCV IRES in all cell lines tested. However, lab IRES still showed increased activity over the control vector, pCMV-GalLuc. Thus, this experiment demonstrates that the lab IRES may be functional in mammalian cells, although its activity is higher in *Drosophila* cells, suggesting that the *Drosophila* cell lines provide the more proper factors for lab IRES function do than mammalian cell lines.

TABLE 1

Lab IRES Activity in Drosophila Kc and Mammalian Cells
Normalized IRES Activity (SD)

| Bicistronic nucleic acid vector | Kc | HeLa | COS-1 | 293 | 3T3 |
| --- | --- | --- | --- | --- | --- |
| pAcGalLuc | 1 (0.04) | ND | ND | ND | ND |
| pAcGalEMCVLuc | 0.31 (0.01) | ND | ND | ND | ND |
| pAcGalAntpLuc | 16.40 (0.63) | ND | ND | ND | ND |
| pAcGalLabLuc | 15.96 (0.59) | ND | ND | ND | ND |
| pCMVGalLuc | ND | 1 (0.02) | 1 (0.01) | 1 (0.11) | 1 (0.06) |
| pCMVGalEMCVLuc | ND | 9.55 (0.16) | 7.26 (0.21) | 7.29 (0.52) | 19.38 (0.52) |
| pCMVGalhBipLuc | ND | 3.21 (0.13) | 1.74 (0.04) | 1.21 (0.17) | 3.19 (0.12) |
| pCMVGalLabLuc | ND | 1.49 (0.08) | 1.60 (0.07) | 1.14 (0.08) | 2.99 (0.08) |

EXAMPLE 6

A Human Homolog of the lab IRES

The lab gene is evolutionarily conserved in humans as the human Homeobox A1. To determine whether the IRES function of lab 5'UTR is also evolutionarily conserved in the human homolog, the putative 5'UTR of Homeobox A1 was analyzed. The putative 5'UTR is 244 nucleotides (SEQ ID NO. 2) and shows 70% similarity and 49% identity with the lab 5'UTR (FIG. 4A). Using Zucker's RNA folding program described in Example 2, the Homeobox A1 5'UTR was predicted to fold into a Y stem-loop structure, similar to that of the lab 5'UTR (FIG. 4B). The similarity in structures of the lab and Homeobox A1 5'UTRs suggested that IRES activity may also be conserved in the human homolog.

Figure 5A:
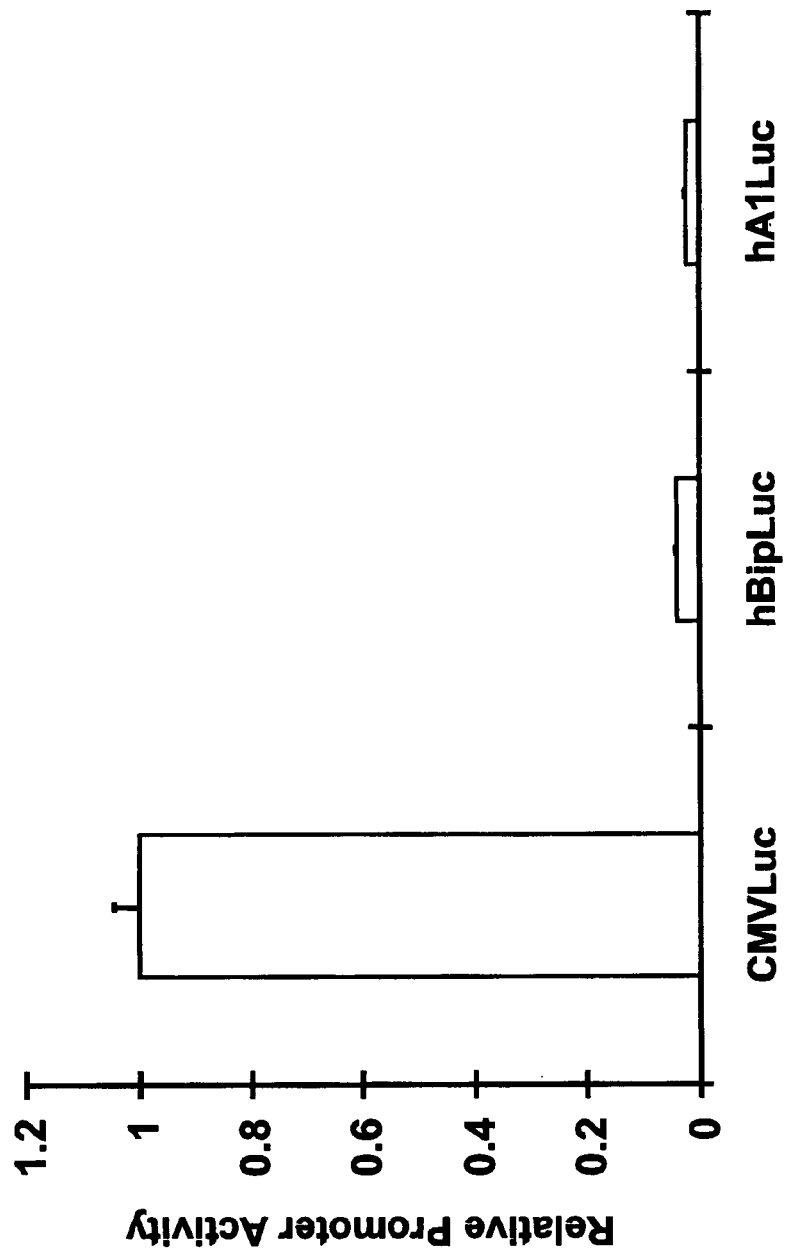
FIG. 5A shows relative promoter activity in HeLa cells transfected with monocistronic vectors pCMV-Luc, phBipLuc, and phA1Luc.

The 5'UTR of Homeobox A1 was first examined for promoter activity and cap-dependent translation activity. To this end, a monocistronic vector, pGL3-Basic (Promega), was used to compare promoter activities of the CMV promoter (a positive control), the 5'UTR of Homeobox A1, and the hBip 5'UTR (a negative control because it is known to lack promoter activity). pGL3-Basic contains a coding sequence for luciferase and a cloning site for a promoter or IRES. The CMV promoter, hBip 5'UTR, and the 244-nt Homeobox A1 5'UTR were inserted upstream of the coding sequence for luciferase at the cloning site for a promoter or IRES. The respective monocistronic nucleic acid vectors, pCMVLuc, phBipLuc, and phA1Luc, were transfected into HeLa cells and assayed for luciferase activity according to Example 1. As shown in FIG. 5A, the relative level of luciferase activity from the phA1Luc was comparable to that of phBipLuc, the negative control, while the relative luciferase activity from the CMV promoter was high. This demonstrates that the 5'UTR of Homeobox A1 does not contain promoter activity.

Figure 5B:
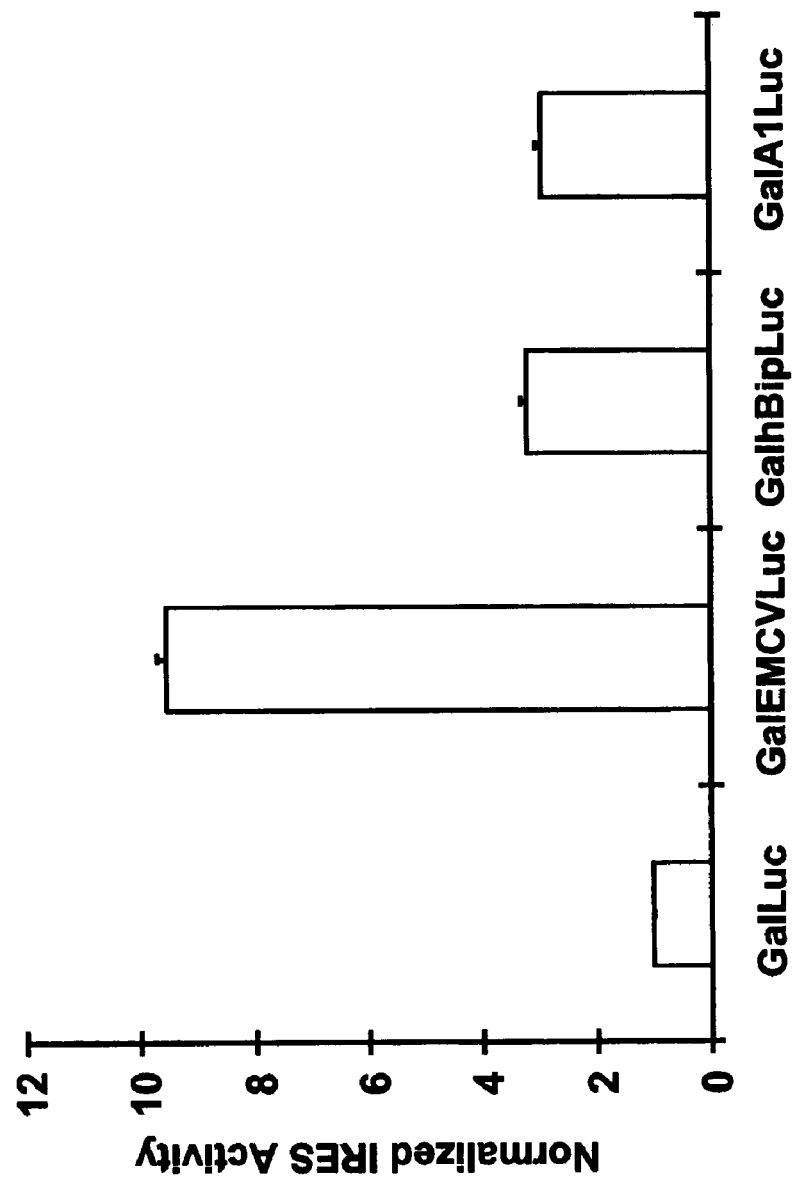
FIG. 5B shows the relative IRES activities in HeLa cells transfected with bicistronic vectors pCMVGalLuc, pCMVGalEMCVLuc, pCMVGalhBipLuc, and pCMVGalA1Luc. CMV represents the cytomegalovirus promoter, hBip represents the human immunoglobulin binding protein IRES, EMCV represents the encephalomyocarditis virus IRES, and A1 represents the Homeobox A1 5'UTR.

The 5'UTR of Homeobox A1 was then analyzed for IRES activity. To this end, the bicistronic vector pCMVGal-Luc described above in Example 5, was utilized. The Homeobox A1 5'UTR was compared with IRESs known to function in mammalian cells: the EMCV IRES and the hBip IRES. The 244-nt 5'UTR of Homeobox A1 and the two known IRES were inserted between the first and second cistrons of pCMVGalLuc to drive the IRES-dependent expression of the luciferase gene. The respective bicistronic nucleic acid vectors, pCMVGalA1Luc, pCMVGalEMCV-Luc, and pCMVGalhBipLuc were transfected into HeLa cells according to Example 1 and IRES activity was measured using the Luc/βGal ratio described in Example 3. As can be seen in FIG. 5B, the A1 5'UTR contained IRES activity comparable to that of hBip IRES, while the EMCV IRES had the strongest IRES activity in HeLa cells.

These experiments demonstrate that the lab and Homeobox A1 genes are evolutionarily conserved not only in protein function but also in IRES activity.

EXAMPLE 7

IRES Activity Requires the Y-type Stem Loop Structure

The Y-type stem loop structure has been identified in some viral and cellular IRESs (Saleh, L., et al., (2001) *J. Gen. Virol.* 82:757–763; Oumard, A., et al., (2000) *Mol. Cell. Biol.* 20:2755–2759; Le, S.-Y., and J. V. Maizel, Jr. (1997) *Nucleic Acids Res.* 25:362–369). The Y-type stem loop structure of the lab IRES was analyzed to determine which regions of the structure are required for IRES activity.

Using the pAcGalLuc bicistronic vector described above in Example 3, deletions and substitutions were made in the lab 5'UTR and are shown in Table 2 below and in FIG. 6A.

TABLE 2

Deletions and Substitutions in the lab IRES

| Remaining lab IRES sequence | Domains Retained | Deletion/Substitition |
| --- | --- | --- |
| Nucleotides 1–239 (full-length) | All | None |
| Nucleotides 1–215 | Domain 1 (1–45) Domain II (46–215) | Domain III (216–239) deleted |
| Nucleotides 45–239 | Domains II and III | Domain I deleted |
| Nucleotides 45–215 | Domain II | Domains I and III deleted |
| Nucleotides 1–74; 187–215 | Domain I Part of Domain II | Part of Domain II deleted Domain III deleted |
| Nucleotides 1–74; 187–239 | Domain I Part of Domain II Domain III | Part of Domain II deleted |

TABLE 2-continued

Deletions and Substitutions in the lab IRES

| Remaining lab IRES sequence | Domains Retained | Deletion/Substitition |
|---|---|---|
| Nucleotides 1–239, with substitution at 124–127 | All | 124–127 nucleotides CCUC substituted with GGGG |

These fragments and variants of the lab IRES were inserted between the first and second cistrons of pAcGalLuc as described in Example 3 above, and transfected into *Drosophila* S2 cells as described in Example 1. IRES activities were measured according to Example 3.

Figure 6A:
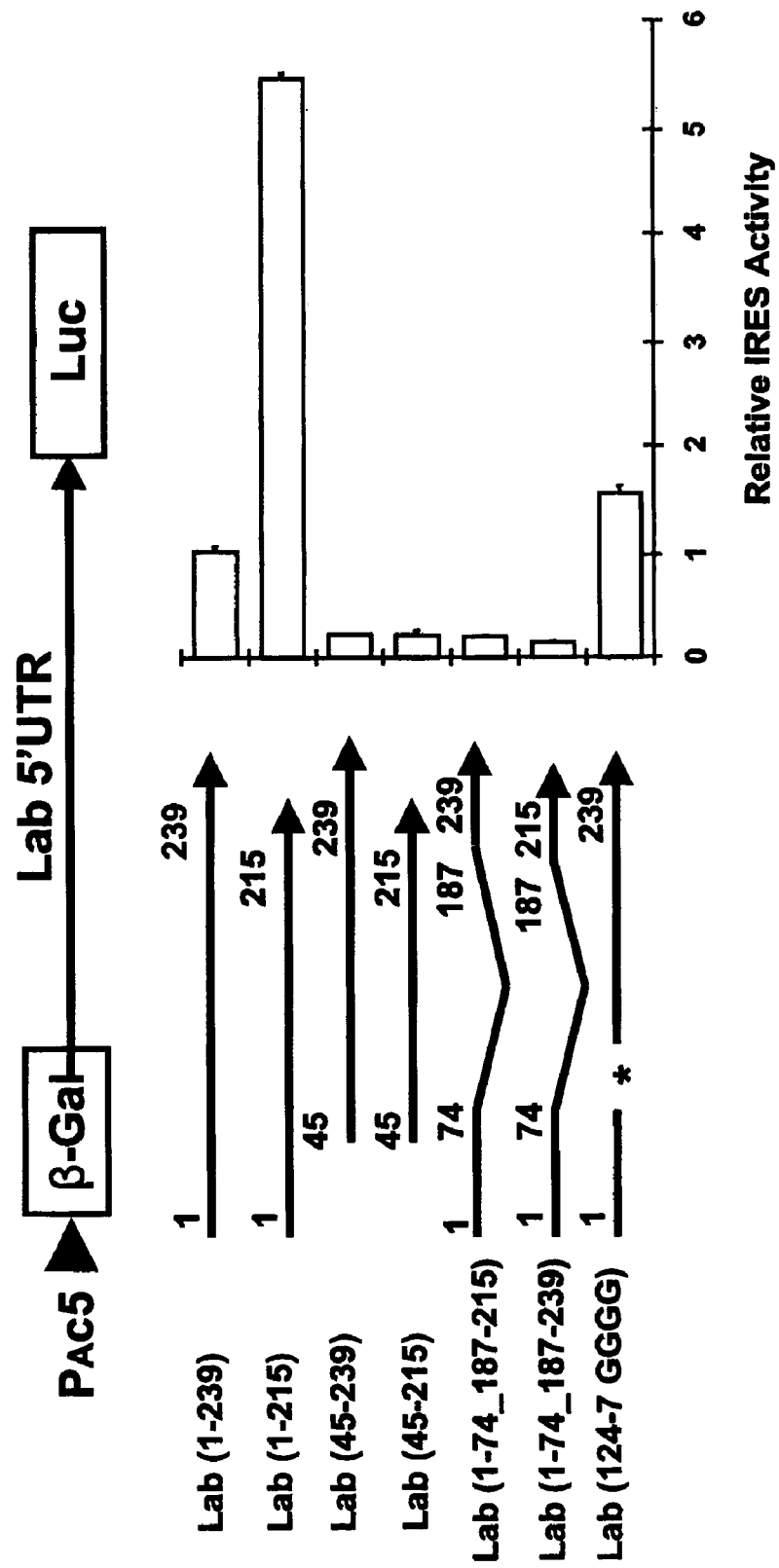
FIG. 6A shows the deletions and mutations of the lab 5'UTR which were inserted into the pAcGalLuc bicistronic vector and tested for IRES activity in Drosophila S2 cells.

As shown in FIG. 6A, deletion of domains I (nt 1–45) or II (nt 46–215) reduced the lab IRES activity dramatically, suggesting that these domains are important for lab IRES activity. Surprisingly, deletion of domain III (nt 216–239) increased lab IRES activity by 5-fold, suggesting that this small hairpin structure may serve as a barrier for IRES-dependent translation.

Figure 6B:
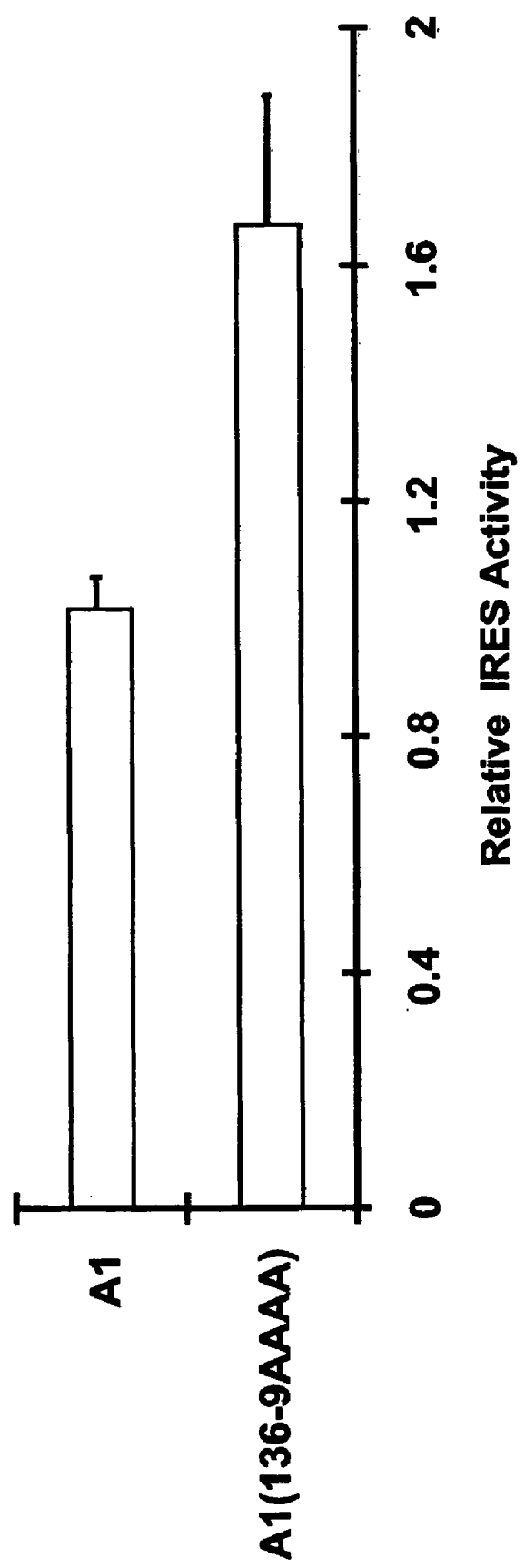
FIG. 6B shows the mutations made in the Homeobox A1 5'UTR at the potential polyprimidine tract binding protein (PTB) binding site and its releative IRES activity in HeLa cells.

A putative polyprimidine tract binding protein (PTB) binding region in lab IRES was mutated to determine if the mutation would disrupt IRES activity. Polyprimidine tract binding protein and other cellular proteins such as La/SSb and unr have been shown to interact with cellular IRESs and modulate IRES-dependent translation in mammalian cells (Holcik, M., and R. G. Korneluk (2000) *Mol. Cell. Biol.* 20:4648–4657; Kim, Y. K., et al., (2000) *J. Mol. Biol.* 304:119–133, Mitchell, S. A., et al., (2001) *Mol. Cell. Biol.* 21:3364–3374). Recently, PTB was identified as playing an important role in neuronal development in *Drosophila* (Dansereau, D., et al., (2001) 42nd Ann. *Drosophila* Res. Conf., abstr. 532A; Davis, M., et al., (2001) 42nd Ann. *Drosophila* Res. Conf., abstr. 357C). Analysis of the lab 5'UTR revealed a potential PTB-binding site (CCUC) at nucleotides 124–127. Similarly, the human homolog of lab, Homeobox A1, also revealed two potential PTB-binding sites in its 5'UTR at nucleotides 136–139 (TCTT) and at 126–129 (CCGC). The potential PTB-binding site in the lab IRES (nt 124–127) was substituted from CCUC to GGGG and one of the potential PTB-binding sites in the Homeobox A1 IRES (nt 136–139) was substituted from TCTT to AAAA (FIGS. 6A and 6B). Interestingly, both mutated IRESs increased IRES activity by about 60–70% (FIGS. 6A and 6B), suggesting that disruption of the PTB binding site on the lab IRES and Homeobox A1 IRES increases IRES activity. This further suggests that PTB acts as a repressor of IRES activity in both lab and Homeobox A1 and that at least some regulatory mechanisms of IRES activity in the lab and Homeobox A1 are also evolutionarily conserved.

EXAMPLE 8

The lab IRES is Useful for Generating Stable Cell Lines

Conventional methods for establishing cell lines that stably produce a recombinant protein of interest require the simultaneous transfection of two monocistronic nucleic acid vectors: one capable of expressing the recombinant protein of interest and another expressing a drug resistance gene that would enable the selection of cells that have acquired potentially both vectors. The drawbacks of co-transfecting two separate nucleic acid vectors include the possibility that a cell would acquire only one of the two vectors and therefore, drug selection would not adequately provide stable cell lines that acquired the vector capable of producing the recombinant protein. It was thus speculated that stable cell lines may be more efficiently generated if both the recombinant protein and drug resistance marker are expressed from the same vector.

Figure 7:
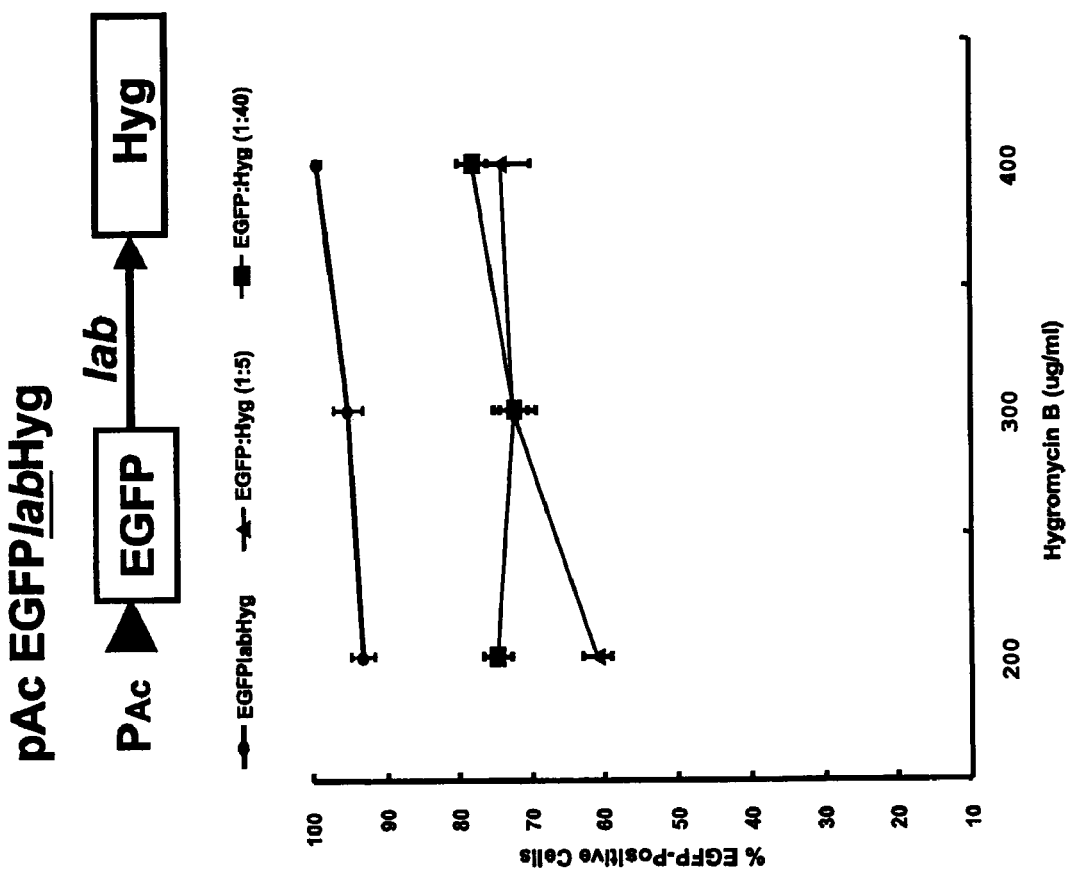
FIG. 7 FIG. 7 illustrates the percentage of Drosophila S2 cells expressing the EGFP protein at three weeks after transfection with the bicistronic vector pAcEGFPlabHyg. Hyg represents a drug resistance gene to hygromycin. The transfected cells were treated with either 200, 300, 400 ug/ml of hygromycin. EGFP expression was also compared with Drosophila S2 cells transfected simultaneously with two monocistronic vectors (pAcEGFP and pCoHygro) at different ratios.

To test the bicistronic expression system in the production of stable cell lines, the pAcEGFPlabHyg nucleic acid vector was constructed. The *Drosophila* actin 5C distal promoter drives the mRNA synthesis of the nucleotide sequence coding for the enhanced green fluorescent protein (EGFP) and hybromycin genes. The lab IRES was inserted between the two cistrons to drive the IRES-dependent translation of the hygromycin gene. This expression construct was transfected into the *Drosophila* S2 cells according to Example 1. For parallel comparison, the EGFP and hygromycin-resistance genes were also transfected into *Drosophila* S2 cells using two separate monocistronic vectors, pAcEGFP and pCoHygro, respectively. The transfected cells were placed in hygromycin-containing medium (200 ug/ml, 300 ug/ml, or 400 ug/ml) for three weeks, at which time the percentage of EGFP-expressing cells was determined. As shown in FIG. 7, 93%, 95%, and 98% of the cells at hygromycin concentrations of 200 ug/ml, 300 ug/ml, or 400 ug/ml, respectively, expressed EGFP when they were transfected with the bicistronic nucleic acid vector expressing both EGFP and the hygromycin-resistance gene. In contrast, only 60–76% of the cells expressed EGFP when they were transfected with two monocistronic nucleic acid vectors. Altering the ratio of the two monocistronic nucleic acid vectors did not appear to significantly increase the percentage of cells expressing EGFP (FIG. 7). Thus, these experiments indicate that the lab IRES bicistronic/multicistronic expression system is a powerful tool for efficient generation of stable cell lines.

EXAMPLE 9

The lab IRES is Useful for Bicistronic/Multicistronic Protein Expression in the Baculovirus Expression System To date, no IRES element has been shown to be functional in the baculovirus expression system. The lab IRES was therefore tested in the baculovirus expression system.

First, the lab IRES was tested for IRES activity in baculovirus host cells, rationalizing that the lab IRES must have IRES activity in baculovirus host cells to be useful in a baculovirus expression system. Bicistronic nucleic acid vectors were constructed from the control pOpIE2GalLuc vector. In pOpIE2GalLuc, the Orgyia pseudotsugata multicapsid nucleopolyhedrosisvirus immediate-early 2 (OpIE2) promoter drives the mRNA synthesis of the nucleotide sequence containing the β-galactosidase and luciferase genes. No promoter or IRES sequences are inserted between the β-galactosidase and luciferase genes. Therefore, it would be expected that the luciferase gene may be translated at low levels or not at all. The EMCV IRES, lab IRES, and Δlab IRES were inserted between the first cistron and second cistron for IRES-dependent translation of the luciferase gene. Δlab IRES comprises nucleotides 1–215 and lacks domain III of the full-length lab IRES, but was shown to have higher IRES activity in *Drosophila* S2 cells (Example 7). The four bicistronic vectors, pOpIE2GalLuc (control), pOpIE2GalEMCVLuc, pOpIE2GallabLuc, and pOpIE2GalΔlabLuc (FIG. 8A), were transfected into baculovirus host insect cells Sf9, Sf21, and High Five™ cells (Invitrogen) according to Example 1. IRES activity was measured according to Example 3. The lab IRES had 23-fold, 37-fold, and 14-fold greater IRES activity than the control in Sf9, Sf21, and High Five cells, respectively (FIGS. 8B, 8C, and 8D, respectively). Notably, the EMCV IRES did not function in any of the baculovirus host cells while the Δlab IRES exhibited IRES activity in all of these cells, albeit slightly less than its full-length counterpart.

Figure 9A:
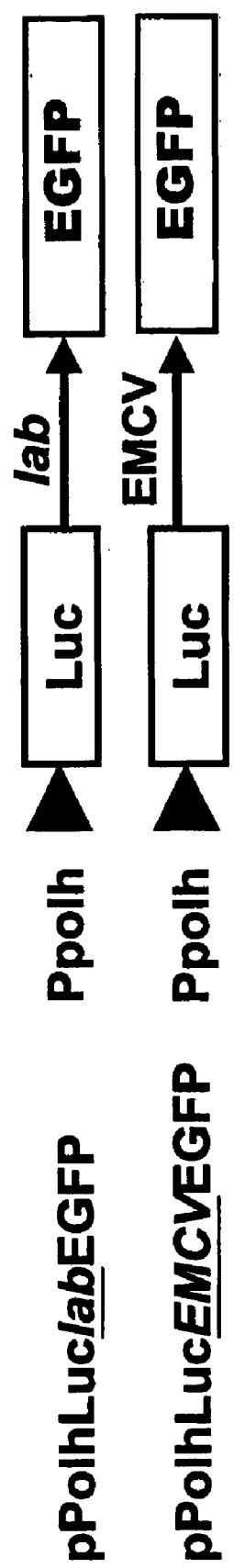
FIG. 9A is a schematic representation of the bicistronic vectors pPolhLuclabEGFP and pPolhLucEMCVEGFP used to generate recombinant baculoviruses. Polh represents the baculovirus polyhedrin promoter.

To generate a recombinant baculovirus carrying a bicistronic/multicistronic nucleic acid vector that may be transferred to and expressed in a baculovirus host cell, the bicistronic transfer control vector, pPolhLucEGFP was used to create bicistronic transfer vectors containing the EMCV and lab IRES. In pPolhLucEGFP, the baculovirus polyherin promoter (Pol) drives the mRNA synthesis of the nucleotide sequence containing the luciferase gene and EGFP genes. There are no promoter or IRES sequences between the first and second cistrons, and therefore, the enhanced green fluorescent protein (EGFP) may be translated at low levels or not at all. The EMCV and lab IRESs are inserted between the first and second cistrons for the IRES-dependent expression of the EGFP gene, creating bicistronic baculovirus transfer vectors pPolhLucEMCVEGFP and pPolhLuclabEGFP, respectively (FIG. 9A). Recombinant baculoviruses were created using the BacPAK™ system from Clontech. Baculovirus host cells, Sf21 cells, were infected with recombinant viruses carrying the pPolhLucEGFP, pPolhLuclabEGFP, or pPolhLucEMCVEGFP for 36 hours, at which time the cells were lysed and assayed for IRES activity using the EGFP/Luc ratio determined according to Example 3. As shown in FIG. 9B, the the lab IRES was active in the baculovirus expression system while the EMCV IRES was again inactive.

It is often desirable to isolate viral plaques because each plaque is the result of a cell being infected by a single recombinant baculovirus. It has been especially difficult in the baculovirus system to select for such plaques because they are usually visualized by overlaying the infected cells with agar. This overlay makes isolation of infected cells time-consuming and difficult. It was speculated that the use of a functional IRES and a bicistronic/multicistronic vector may enhance the isolation of cell lines expressing the protein of interest. Sf21 cells were infected with recombinant baculovirus carrying the pPolhLuclabEGFP vector for 2 days, after which time the cells were analyzed by fluorescent microscopy for luciferase and EGFP expression. As shown in FIG. 10, cells infected with the recombinant baculovirus formed plaques which could be visualized by EGFP expression. All of the EGFP-positive plaques also expressed luciferase (not shown). In this manner, cells expressing the desired protein could be easily detected and isolated, avoiding the time-consuming traditional method of plaque assays.

The specification is most thoroughly understood in light of the teachings of the references cited within the specification, all of which are hereby incorporated by reference in their entirety. The embodiments within the specification provide an illustration of embodiments of the invention and should not be construed to limit the scope of the invention. The skilled artisan recognizes that many other embodiments are encompassed by the claimed invention and that it is intended that the specification and examples be considered as exemplary only, with the true scope and spirit of the invention being indicated by the following claims.

We claim:

1. A nucleic acid vector for the expression of at least two cistrons comprising:
   a. a promoter operably linked to a nucleotide sequence comprising at least two cistrons; and
   b. a nucleotide sequence that provides IRES activity operably linked to each cistron subsequent to the first cistron, wherein at least one of the nucleotide sequences that provide IRES activity comprises a nucleotide sequence chosen from:
   a nucleotide sequence comprising SEQ ID NO. 1;
   a nucleotide sequence comprising nucleotides 1–215 of SEQ ID NO. 1;
   a nucleotide sequence comprising nucleotides 45–239 of SEQ ID NO. 1;
   a nucleotide sequence comprising nucleotides 45–215 of SEQ ID NO. 1;
   a nucleotide sequence comprising nucleotides 1–74 and 187–239 of SEQ ID NO. 1;
   a nucleotide sequence comprising nucleotides 1–74 and 187–215 of SEQ ID NO. 1;
   a nucleotide sequence that differs from a nucleotide sequence comprising SEQ ID NO. 1 by substitution of the nucleotides at positions 124–127 of SEQ ID NO. 1;
   a nucleotide sequence comprising SEQ ID NO. 2;
   a nucleotide sequence that differs from a nucleotide sequence comprising SEQ ID NO. 2 by substitution of the nucleotides at positions 136–139 of SEQ ID NO. 2; and
   a nucleotide sequence that differs from a nucleotide sequence comprising SEQ ID NO. 2 by substitution of the nucleotides at positions 126–129 of SEQ ID NO. 2.

2. The nucleic acid vector of claim 1, wherein at least one of said at least two cistrons comprises a reporter gene.

3. The nucleic acid vector of claim 1, wherein at least one of said at least two cistrons comprises a therapeutic gene.

4. A biological vector capable of expressing at least two cistrons comprising the nucleic acid vector of claim 1.

5. The biological vector of claim 4, wherein said biological vector is selected from poxvirus, adenovirus, herpesvirus, adeno-associated virus, retrovirus, and baculovirus.

6. A host cell comprising the nucleic acid vector of claim 1.

7. The host cell of claim 6, wherein said host cell is an insect cell.

8. The host cell of claim 7, wherein said insect cell is a Drosophila cell.

9. A method for expressing at least two cistrons comprising: introducing into a host cell a nucleic acid vector comprising:
   a. a promoter operably linked to a nucleotide sequence comprising at least two cistrons; and
   b. a nucleotide sequence that provides IRES activity operably linked to each cistron subsequent to the first cistron, wherein at least one of the nucleotide sequences that provide IRES activity comprises a nucleotide sequence chosen from:
   a nucleotide sequence comprising SEQ ID NO. 1;
   a nucleotide sequence comprising nucleotides 1–215 of SEQ ID NO. 1;
   a nucleotide sequence comprising nucleotides 45–239 of SEQ ID NO. 1;
   a nucleotide sequence comprising nucleotides 45–215 of SEQ ID NO. 1;
   a nucleotide sequence comprising nucleotides 1–74 and 187–239 of SEQ ID NO. 1;
   a nucleotide sequence comprising nucleotides 1–74 and 187–215 of SEQ ID NO. 1;
   a nucleotide sequence that differs from a nucleotide sequence comprising SEQ ID NO. 1 by substitution of the nucleotides at positions 124–127 of SEQ ID NO. 1;
   a nucleotide sequence comprising SEQ ID NO. 2;
   a nucleotide sequence that differs from a nucleotide sequence comprising SEQ ID NO. 2 by substitution of the nucleotides at positions 136–139 of SEQ ID NO. 2; and
   a nucleotide sequence that differs from a nucleotide sequence comprising SEQ ID NO. 2 by substitution of the nucleotides at positions 126–129 of SEQ ID NO. 2.

10. A baculovirus transfer vector for the expression of at least two cistrons comprising:
    a. a polyhedrin promoter operably linked to a nucleotide sequence comprising at least two cistrons; and
    b. a nucleotide sequence that provides IRES activity operably linked to each cistron subsequent to the first cistron, wherein at least one of the nucleotide sequences that provide IRES activity comprises a nucleotide sequence chosen from:
    a nucleotide sequence comprising SEQ ID NO. 1;
    a nucleotide sequence comprising nucleotides 1–215 of SEQ ID NO. 1;
    a nucleotide sequence comprising nucleotides 45–239 of SEQ ID NO. 1;
    a nucleotide sequence comprising nucleotides 45–215 of SEQ ID NO. 1;
    a nucleotide sequence comprising nucleotides 1–74 and 187–239 of SEQ ID NO. 1;
    a nucleotide sequence comprising nucleotides 1–74 and 187–215 of SEQ ID NO. 1;
    a nucleotide sequence that differs from a nucleotide sequence comprising SEQ ID NO. 1 by substitution of the nucleotides at positions 124–127 of SEQ ID NO. 1;
    a nucleotide sequence comprising SEQ ID NO. 2;
    a nucleotide sequence that differs from a nucleotide sequence comprising SEQ ID NO. 2 by substitution of the nucleotides at positions 136–139 of SEQ ID NO. 2; and
    a nucleotide sequence that differs from a nucleotide sequence comprising SEQ ID NO. 2 by substitution of the nucleotides at positions 126–129 of SEQ ID NO. 2.

11. The baculovirus transfer vector of claim 10, wherein at least one of at least two cistrons comprises a reporter gene.

12. The baculovirus transfer vector of claim 10, wherein at least one of at least two cistrons comprises a therapeutic gene.

13. A recombinant baculovirus capable of expressing at least two cistrons in a host cell comprising a baculovirus genome comprising:
    a. a polyhedrin promoter operably linked to a nucleotide sequence comprising at least two cistrons; and
    b. a nucleotide sequence that provides IRES activity operably linked to each cistron subseauent to the first cistron, wherein at least one of the nucleotide sequences that provide IRES activity comprises a nucleotide sequence chosen from:
    a nucleotide sequence comprising SEQ ID NO. 1;
    a nucleotide sequence comprising nucleotides 1–215 of SEQ ID NO. 1;
    a nucleotide sequence comprising nucleotides 45–239 of SEQ ID NO. 1;
    a nucleotide sequence comprising nucleotides 45–215 of SEQ ID NO. 1;

a nucleotide sequence comprising nucleotides 1–74 and 187–239 of SEQ ID NO. 1;
a nucleotide sequence comprising nucleotides 1–74 and 187–215 of SEQ ID NO. 1;

a nucleotide sequence that differs from a nucleotide sequence comprising SEQ ID NO. 1 by substitution of the nucleotides at positions 124–127 of SEQ ID NO. 1;

a nucleotide sequence comprising SEQ ID NO. 2;

a nucleotide sequence that differs from a nucleotide sequence comprising SEQ ID NO. 2 by substitution of the nucleotides at positions 136–139 of SEQ ID NO.2; and a nucleotide sequence that differs from a nucleotide sequence comprising SEQ ID NO. 2 by substitution of the nucleotides at positions 126–129 of SEQ ID NO. 2.

14. An in vitro method for producing a recombinant baculovirus capable of expressing at least two cistrons comprising:

a. introducing a baculovirus transfer vector of claim 10 and a baculovirus genomic DNA into a baculovirus host cell so as to effect homologous recombination; and b. isolating a recombinant baculovirus.

15. The method of claim 14, wherein said recombinant baculovirus is isolated by selecting plaques expressing at least one of said at least two cistrons.

16. A baculovirus host cell expressing at least two cistrons comprising the recombinant baculovirus of claim 13.

* * * * *

UNITED STATES PATENT AND TRADEMARK OFFICE
CERTIFICATE OF CORRECTION

PATENT NO.       : 7,119,187 B2
APPLICATION NO.  : 10/614282
DATED            : October 10, 2006
INVENTOR(S)      : Lee et al.

It is certified that error appears in the above-identified patent and that said Letters Patent is hereby corrected as shown below:

Claim 4, column 23, line 37, "biological" should read --viral--.

Claim 5, column 23, line 39, "biological" should read --viral--.

lines 39-40, "biological" should read --viral--.

Claim 6, column 23, line 42, "A host" should read --An isolated eukaryotic host--.

Claim 9, column 23, line 48, "A method" should read --An *in vitro* method--.

Claim 13, column 24, line 52, "a host" should read --an isolated host--.

line 57, "subseauent" should read --subsequent--.

Claim 16, column 26, line 11, "A baculovirus" should read --An isolated baculovirus--.

Signed and Sealed this

Twenty-sixth Day of December, 2006

JON W. DUDAS
*Director of the United States Patent and Trademark Office*

SEQUENCE LISTING

<160> NUMBER OF SEQ ID NOS: 2

<210> SEQ ID NO 1
<211> LENGTH: 239
<212> TYPE: DNA
<213> ORGANISM: Drosophila labial

<400> SEQUENCE: 1

```
atcagtcacg acttggtaag cgcgcaggca gcacgtcgtc gtcgtcatcg ccaacgggag      60
tcgtgttttt cggttcgata cagataaaac ccacgtcgat agccctcgac cgtcgcgtaa     120
tattcttaga aagcaaacag ctaaagaact atttcaagaa ctgtgtggca agtgaagggt     180
agttagtgat acaccggtta tatcggagtg gcgagaaagt gtggttccgg ctggacaat      239
```

<210> SEQ ID NO 2
<211> LENGTH: 244
<212> TYPE: DNA
<213> ORGANISM: Homo sapiens

<400> SEQUENCE: 2

```
agcgccgggg atttaaatgc cactaaaacg gtgatccatc actgcggaag ccggcaaact      60
tttgcaggag gctcagccat tggctgacac cgtcacgtgc ccctcctcca gcgtcctccg     120
ccctcccgcc ccccctcttg cgcactgtac attcatatca tttttcttct ccggcccat     180 ggaggaagtg agaaagttgg cacagtcacg ccgggcttcg caggaccagg tcactcagtg     240
acag                                                                   244
```